(12) United States Patent
Hoffman et al.

(10) Patent No.: US 11,967,406 B2
(45) Date of Patent: *Apr. 23, 2024

(54) MULTI-SITE CLINICAL DECISION SUPPORT

(71) Applicant: CERNER INNOVATION, INC., North Kansas City, MO (US)

(72) Inventors: Mark A. Hoffman, Lee's Summit, MO (US); Hugh Ryan, Lee's Summit, MO (US); Bharat Sutariya, Parkville, MO (US); Leo V. Perez, Platte City, MO (US); John Kuckelman, Shawnee, KS (US)

(73) Assignee: Cerner Innovation, Inc., North Kansas City, MO (US)

( * ) Notice: Subject to any disclaimer, the term of this patent is extended or adjusted under 35 U.S.C. 154(b) by 81 days.

This patent is subject to a terminal disclaimer.

(21) Appl. No.: 17/693,738

(22) Filed: Mar. 14, 2022

(65) Prior Publication Data

US 2022/0199210 A1 Jun. 23, 2022

Related U.S. Application Data

(63) Continuation of application No. 13/269,244, filed on Oct. 7, 2011, now Pat. No. 11,348,667.
(Continued)

(51) Int. Cl.
*G16H 10/60* (2018.01)
*G16H 15/00* (2018.01)
(Continued)

(52) U.S. Cl.
CPC .............. *G16H 10/60* (2018.01); *G16H 40/67* (2018.01); *G16H 50/20* (2018.01); *G16H 15/00* (2018.01)

(58) Field of Classification Search
CPC ........ G16H 10/60; G16H 40/67; G16H 50/20; G16H 15/00; G16H 50/30
See application file for complete search history.

(56) References Cited

U.S. PATENT DOCUMENTS

| 4,839,853 A | 6/1989 | Deerwester et al. |
| 5,243,565 A | 9/1993 | Yamamoto |
| (Continued) | | |

FOREIGN PATENT DOCUMENTS

| EP | 1043666 A2 | 10/2000 |
| EP | 2365456 A2 | 9/2011 |
| (Continued) | | |

OTHER PUBLICATIONS

Chung, Impact of extravascular lung water index on outcomes of severe sepsis patients in a medical intensive care unit, 2008, Respiratory Medicine, pp. 956-961. (Year: 2008).*

(Continued)

*Primary Examiner* — Christopher L Gilligan
(74) *Attorney, Agent, or Firm* — Kilpatrick Townsend & Stockton LLP

(57) ABSTRACT

Methods are provided for the surveillance and monitoring of a patient's medical care when the patient is treated at two or more medical organizations having different medical record systems. Patient information is received from a first medical organization and populated into an active risk assessment array that monitors the patient's risk for developing a particular disease or condition. Patient information is then received from a second medical organization and populated into the array. It is determined that actionable criteria have been met, and in response, a notification or alert is sent to the medical organizations indicating that the patient is at risk.

18 Claims, 16 Drawing Sheets

Related U.S. Application Data

(60) Provisional application No. 61/391,392, filed on Oct. 8, 2010.

(51) Int. Cl.
*G16H 40/67* (2018.01)
*G16H 50/20* (2018.01)

(56) References Cited

U.S. PATENT DOCUMENTS

| | | |
|---|---|---|
| 5,301,109 A | 4/1994 | Landauer et al. |
| 5,664,109 A | 9/1997 | Johnson et al. |
| 5,809,494 A | 9/1998 | Nguyen |
| 5,835,900 A | 11/1998 | Fagg et al. |
| 6,039,688 A | 3/2000 | Douglas et al. |
| 6,122,628 A | 9/2000 | Castelli et al. |
| 6,246,964 B1 | 6/2001 | Blaunstein |
| 6,246,975 B1 | 6/2001 | Rivonelli et al. |
| 6,247,004 B1 | 6/2001 | Moukheibir |
| 6,397,224 B1 | 5/2002 | Zubeldia et al. |
| 6,618,715 B1 | 9/2003 | Johnson et al. |
| 6,654,740 B2 | 11/2003 | Tokuda et al. |
| 6,665,669 B2 | 12/2003 | Han et al. |
| 6,915,254 B1 | 7/2005 | Heinze et al. |
| 6,996,575 B2 | 2/2006 | Cox et al. |
| 7,039,634 B2 | 5/2006 | Xu et al. |
| 7,120,626 B2 | 10/2006 | Li et al. |
| 7,249,117 B2 | 7/2007 | Estes |
| 7,386,522 B1 | 6/2008 | Bigus et al. |
| 7,440,947 B2 | 10/2008 | Adcock et al. |
| 7,447,643 B1 | 11/2008 | Olson et al. |
| 7,496,561 B2 | 2/2009 | Caudill et al. |
| 7,529,765 B2 | 5/2009 | Brants et al. |
| 7,555,425 B2 | 6/2009 | Oon |
| 7,558,778 B2 | 7/2009 | Carus et al. |
| 7,617,078 B2 | 11/2009 | Rao et al. |
| 7,640,171 B2 | 12/2009 | Gendron et al. |
| 7,657,540 B1 | 2/2010 | Bayliss |
| 7,668,820 B2 | 2/2010 | Zuleba |
| 7,720,846 B1 | 5/2010 | Bayliss |
| 7,831,423 B2 | 11/2010 | Schubert |
| 7,844,449 B2 | 11/2010 | Lin et al. |
| 7,844,566 B2 | 11/2010 | Wnek |
| 7,853,456 B2 | 12/2010 | Soto et al. |
| 7,865,373 B2 | 1/2011 | Punzak et al. |
| 7,899,764 B2 | 3/2011 | Martin et al. |
| 7,899,796 B1 | 3/2011 | Borthwick et al. |
| 7,900,052 B2 | 3/2011 | Jonas |
| 7,912,842 B1 | 3/2011 | Bayliss |
| 7,933,909 B2 | 4/2011 | Trepetin |
| 7,953,685 B2 | 5/2011 | Liu et al. |
| 8,015,136 B1 | 9/2011 | Baker et al. |
| 8,078,554 B2 | 12/2011 | Fung et al. |
| 8,126,736 B2 | 2/2012 | Anderson et al. |
| 8,160,895 B2 | 4/2012 | Schmitt et al. |
| 8,165,893 B1 | 4/2012 | Goldberg et al. |
| 8,200,505 B2 | 6/2012 | Walker et al. |
| 8,439,835 B1 * | 5/2013 | McKinley .............. G16H 10/60 128/920 |
| 8,515,777 B1 | 8/2013 | Rajasenan |
| 8,539,424 B2 | 9/2013 | Tetelbaum |
| 8,589,424 B1 | 11/2013 | Patel et al. |
| 8,666,785 B2 | 3/2014 | Baluta et al. |
| 8,838,628 B2 | 9/2014 | Leighton et al. |
| 8,856,156 B1 | 10/2014 | Mcnair et al. |
| 9,375,142 B2 | 6/2016 | Schultz et al. |
| 9,542,532 B1 | 1/2017 | Mcnair et al. |
| 9,542,647 B1 | 1/2017 | Mirhaji |
| 9,734,146 B1 | 8/2017 | Mcnair et al. |
| 10,198,499 B1 | 2/2019 | Mcnair et al. |
| 10,249,385 B1 | 4/2019 | Mcnair et al. |
| 10,268,687 B1 | 4/2019 | Douglas |
| 10,431,336 B1 | 10/2019 | Murrish et al. |
| 10,446,273 B1 | 10/2019 | Mcnair et al. |
| 10,483,003 B1 | 11/2019 | Mcnair et al. |
| 10,580,524 B1 | 3/2020 | Mcnair et al. |
| 10,769,241 B1 | 9/2020 | Mcnair |
| 10,854,334 B1 | 12/2020 | Mcnair et al. |
| 10,946,311 B1 | 3/2021 | Mcnair |
| 10,957,449 B1 | 3/2021 | Mcnair et al. |
| 11,100,933 B2 | 8/2021 | Lefkofsky et al. |
| 2002/0007284 A1 | 1/2002 | Schurenberg et al. |
| 2002/0023067 A1 | 2/2002 | Garland et al. |
| 2002/0032583 A1 | 3/2002 | Joao |
| 2002/0035486 A1 | 3/2002 | Huyn et al. |
| 2002/0038227 A1 | 3/2002 | Fey et al. |
| 2002/0038308 A1 | 3/2002 | Cappi |
| 2002/0042793 A1 | 4/2002 | Choi |
| 2002/0073138 A1 | 6/2002 | Gilbert et al. |
| 2002/0128860 A1 * | 9/2002 | Leveque .............. G16H 70/60 705/2 |
| 2003/0023571 A1 | 1/2003 | Barnhill |
| 2003/0038308 A1 | 2/2003 | Kim |
| 2003/0055679 A1 | 3/2003 | Soll et al. |
| 2003/0163057 A1 | 8/2003 | Flick et al. |
| 2003/0212580 A1 | 11/2003 | Shen |
| 2004/0199332 A1 | 10/2004 | Iliff |
| 2004/0230105 A1 | 11/2004 | Geva et al. |
| 2004/0260666 A1 | 12/2004 | Pestotnik et al. |
| 2005/0027562 A1 | 2/2005 | Brown |
| 2005/0049497 A1 | 3/2005 | Krishnan et al. |
| 2005/0055246 A1 | 3/2005 | Simon |
| 2005/0119534 A1 | 6/2005 | Trost et al. |
| 2005/0144042 A1 | 6/2005 | Joffe et al. |
| 2005/0256740 A1 | 11/2005 | Kohan et al. |
| 2005/0272984 A1 | 12/2005 | Huiku |
| 2005/0288910 A1 | 12/2005 | Schlessinger et al. |
| 2006/0020465 A1 | 1/2006 | Cousineau et al. |
| 2006/0036619 A1 * | 2/2006 | Fuerst .................... G16H 50/80 |
| 2006/0064447 A1 | 3/2006 | Malkov |
| 2006/0074824 A1 | 4/2006 | Li |
| 2006/0129427 A1 | 6/2006 | Wennberg |
| 2006/0161457 A1 | 7/2006 | Rapaport et al. |
| 2006/0173663 A1 | 8/2006 | Langheier et al. |
| 2006/0205564 A1 | 9/2006 | Peterson |
| 2006/0206027 A1 | 9/2006 | Malone |
| 2006/0206359 A1 | 9/2006 | Stang |
| 2006/0218010 A1 | 9/2006 | Michon et al. |
| 2006/0271556 A1 | 11/2006 | Mukherjee et al. |
| 2007/0005621 A1 | 1/2007 | Lesh et al. |
| 2007/0026365 A1 | 2/2007 | Friedrich et al. |
| 2007/0031873 A1 | 2/2007 | Wang et al. |
| 2007/0094048 A1 | 4/2007 | Grichnik |
| 2007/0106533 A1 | 5/2007 | Greene |
| 2007/0106752 A1 | 5/2007 | Moore |
| 2007/0233391 A1 | 10/2007 | Milstein et al. |
| 2007/0239482 A1 | 10/2007 | Finn et al. |
| 2007/0244724 A1 | 10/2007 | Pendergast et al. |
| 2008/0021288 A1 | 1/2008 | Bowman et al. |
| 2008/0046292 A1 | 2/2008 | Myers et al. |
| 2008/0097938 A1 | 4/2008 | Guyon et al. |
| 2008/0131374 A1 | 6/2008 | Medich et al. |
| 2008/0133269 A1 | 6/2008 | Ching |
| 2008/0147438 A1 | 6/2008 | Kil |
| 2008/0147441 A1 | 6/2008 | Kil |
| 2008/0172214 A1 | 7/2008 | Col et al. |
| 2008/0172251 A1 | 7/2008 | Reichert et al. |
| 2008/0183454 A1 | 7/2008 | Barabasi et al. |
| 2008/0195422 A1 | 8/2008 | Nessinger et al. |
| 2008/0243548 A1 | 10/2008 | Cafer |
| 2008/0249376 A1 | 10/2008 | Zaleski |
| 2008/0255884 A1 | 10/2008 | Carus et al. |
| 2008/0256006 A1 | 10/2008 | Buscema et al. |
| 2008/0268413 A1 | 10/2008 | Leichner |
| 2008/0275731 A1 | 11/2008 | Rao et al. |
| 2008/0287746 A1 | 11/2008 | Reisman |
| 2008/0288292 A1 | 11/2008 | Bi et al. |
| 2008/0288474 A1 | 11/2008 | Chin et al. |
| 2008/0294692 A1 | 11/2008 | Angell et al. |
| 2008/0301177 A1 | 12/2008 | Doherty |
| 2008/0306926 A1 | 12/2008 | Friedlander et al. |
| 2009/0006431 A1 | 1/2009 | Agrawal et al. |
| 2009/0012928 A1 | 1/2009 | Lussier et al. |

(56) References Cited

U.S. PATENT DOCUMENTS

| | | |
|---|---|---|
| 2009/0069642 A1* | 3/2009 | Gao .................... H04L 67/125 600/300 |
| 2009/0112892 A1 | 4/2009 | Cardie et al. |
| 2009/0125333 A1 | 5/2009 | Heywood et al. |
| 2009/0132284 A1 | 5/2009 | Fey et al. |
| 2009/0164249 A1 | 6/2009 | Hunt et al. |
| 2009/0228303 A1 | 9/2009 | Faulkner et al. |
| 2009/0259493 A1 | 10/2009 | Venon et al. |
| 2009/0299767 A1 | 12/2009 | Michon et al. |
| 2009/0299977 A1 | 12/2009 | Rosales |
| 2009/0304246 A1 | 12/2009 | Walker et al. |
| 2009/0313041 A1 | 12/2009 | Eder |
| 2009/0318775 A1 | 12/2009 | Michelson et al. |
| 2009/0319295 A1 | 12/2009 | Kass-Hout et al. |
| 2010/0082369 A1 | 4/2010 | Prenelus et al. |
| 2010/0088117 A1 | 4/2010 | Belden et al. |
| 2010/0121883 A1 | 5/2010 | Cutting et al. |
| 2010/0131434 A1 | 5/2010 | Magent et al. |
| 2010/0131438 A1 | 5/2010 | Pandya et al. |
| 2010/0131482 A1 | 5/2010 | Linthicum et al. |
| 2010/0131883 A1 | 5/2010 | Linthicum et al. |
| 2010/0142774 A1 | 6/2010 | Ben-Haim et al. |
| 2010/0145720 A1 | 6/2010 | Reiner |
| 2010/0153133 A1 | 6/2010 | Angell et al. |
| 2010/0179818 A1 | 7/2010 | Kelly et al. |
| 2010/0185685 A1 | 7/2010 | Chew et al. |
| 2010/0198755 A1* | 8/2010 | Soll ....................... G16H 10/60 706/11 |
| 2010/0235330 A1 | 9/2010 | Reiner |
| 2010/0274576 A1 | 10/2010 | Young |
| 2010/0293003 A1 | 11/2010 | Abbo |
| 2010/0299155 A1 | 11/2010 | Findlay et al. |
| 2010/0324861 A1 | 12/2010 | Goulding et al. |
| 2010/0324938 A1 | 12/2010 | Ennett et al. |
| 2011/0010401 A1 | 1/2011 | Adams et al. |
| 2011/0015937 A1 | 1/2011 | Janas et al. |
| 2011/0046979 A1 | 2/2011 | Tulipano et al. |
| 2011/0067108 A1 | 3/2011 | Hoglund |
| 2011/0077973 A1* | 3/2011 | Breitenstein .......... G06F 3/0484 705/3 |
| 2011/0087501 A1 | 4/2011 | Severin |
| 2011/0093467 A1 | 4/2011 | Sharp et al. |
| 2011/0119089 A1 | 5/2011 | Carlisle |
| 2011/0161110 A1 | 6/2011 | Mault |
| 2011/0201900 A1 | 8/2011 | Zhang et al. |
| 2011/0225001 A1 | 9/2011 | Shen |
| 2011/0246238 A1 | 10/2011 | Vdovjak et al. |
| 2011/0270629 A1 | 11/2011 | Abbo |
| 2011/0295621 A1 | 12/2011 | Farooq et al. |
| 2011/0306845 A1 | 12/2011 | Osorio |
| 2012/0016685 A1 | 1/2012 | Ryan et al. |
| 2012/0020536 A1 | 1/2012 | Moehrle |
| 2012/0047105 A1 | 2/2012 | Saigal et al. |
| 2012/0059779 A1 | 3/2012 | Syed et al. |
| 2012/0072235 A1 | 3/2012 | Varadarajan et al. |
| 2012/0078127 A1 | 3/2012 | Mcdonald et al. |
| 2012/0086963 A1 | 4/2012 | Fujitsuka et al. |
| 2012/0089420 A1 | 4/2012 | Hoffman et al. |
| 2012/0095780 A1 | 4/2012 | Mcnair |
| 2012/0109685 A1 | 5/2012 | Carter et al. |
| 2012/0110016 A1 | 5/2012 | Phillips |
| 2012/0173475 A1 | 7/2012 | Ash et al. |
| 2012/0174014 A1 | 7/2012 | Ash et al. |
| 2012/0174018 A1 | 7/2012 | Ash et al. |
| 2012/0175475 A1 | 7/2012 | Mcerlane |
| 2012/0185275 A1 | 7/2012 | Loghmani |
| 2012/0203575 A1 | 8/2012 | Tulipano et al. |
| 2012/0215784 A1 | 8/2012 | King et al. |
| 2012/0232930 A1 | 9/2012 | Schmidt et al. |
| 2012/0246102 A1 | 9/2012 | Sudharsan |
| 2013/0006911 A1 | 1/2013 | Christie et al. |
| 2013/0023434 A1 | 1/2013 | Van |
| 2013/0031613 A1 | 1/2013 | Shanabrook et al. |
| 2013/0046529 A1 | 2/2013 | Grain et al. |
| 2013/0046558 A1 | 2/2013 | Landi et al. |
| 2013/0110547 A1 | 5/2013 | Englund et al. |
| 2013/0110548 A1 | 5/2013 | Kutty |
| 2013/0132308 A1 | 5/2013 | Boss et al. |
| 2013/0132312 A1 | 5/2013 | Lee et al. |
| 2013/0132323 A1 | 5/2013 | Soto et al. |
| 2013/0158968 A1 | 6/2013 | Ash et al. |
| 2013/0197938 A1 | 8/2013 | Bayouk et al. |
| 2013/0245389 A1 | 9/2013 | Schultz et al. |
| 2014/0081652 A1 | 3/2014 | Klindworth |
| 2014/0095184 A1 | 4/2014 | Gotz et al. |
| 2014/0095186 A1 | 4/2014 | Gotz et al. |
| 2014/0180699 A1 | 6/2014 | Massa et al. |
| 2014/0181128 A1 | 6/2014 | Riskin et al. |
| 2014/0200414 A1 | 7/2014 | Osorio |
| 2014/0336539 A1 | 11/2014 | Torres et al. |
| 2015/0049947 A1 | 2/2015 | Katsaros et al. |
| 2015/0161329 A1 | 6/2015 | Mabotuwana et al. |
| 2015/0193583 A1 | 7/2015 | Mcnair et al. |
| 2015/0254408 A1 | 9/2015 | Dadlani Mahtani et al. |
| 2015/0324535 A1 | 11/2015 | Ash et al. |
| 2015/0363559 A1 | 12/2015 | Jackson et al. |
| 2016/0004840 A1 | 1/2016 | Rust et al. |
| 2016/0063212 A1 | 3/2016 | Monier et al. |
| 2016/0143594 A1 | 5/2016 | Moorman et al. |
| 2017/0098358 A1 | 4/2017 | Bechtel et al. |
| 2017/0124269 A1 | 5/2017 | Mcnair et al. |
| 2019/0336085 A1 | 11/2019 | Kayser et al. |
| 2020/0043612 A1 | 2/2020 | Mcnair et al. |
| 2020/0335179 A1 | 10/2020 | Stojadinovic et al. |
| 2021/0177338 A1 | 6/2021 | Pagi et al. |

FOREIGN PATENT DOCUMENTS

| | | | |
|---|---|---|---|
| WO | 2006002465 A1 | 1/2006 | |
| WO | 2009112977 A1 | 9/2009 | |
| WO | WO-2009141359 A1 * | 11/2009 | ......... G01N 33/6893 |
| WO | 2010045463 A2 | 4/2010 | |
| WO | 2012122122 A1 | 9/2012 | |
| WO | 2012122195 A1 | 9/2012 | |
| WO | 2012122196 A2 | 9/2012 | |

OTHER PUBLICATIONS

Non-Final Office Action received for U.S. Appl. No. 16/717,299, dated Apr. 27, 2022, 10 pages.

Non-Final Office Action received for U.S. Appl. No. 16/819,890, dated Apr. 28, 2022, 17 pages.

Notice of Allowance received for U.S. Appl. No. 14/148,039, dated Jul. 11, 2022, 10 pages.

Final Office Action received for U.S. Appl. No. 16/717,299, dated Oct. 27, 2022, 13 pages.

Final Office Action received for U.S. Appl. No. 16/819,890, dated Oct. 27, 2022, 17 pages.

Final Office Action received for U.S. Appl. No. 17/011,474, dated Oct. 12, 2022, 17 pages.

Notice of Allowance received for U.S. Appl. No. 17/387,786, dated Nov. 30, 2022, 16 pages.

The Comprehensive R Archive Network, R, Available online at: <http://cran.r-project.org>, Retrieved on Feb. 27, 2020, 1 page.

Abbott et al., "Sequence Analysis and Optimal Matching Methods in Sociology, Review and Prospect", Sociol Meth Res, vol. 29, 2000, pp. 3-33.

Abernethy et al., "Eliciting Consumer Preferences Using Robust Adaptive Choice Questionnaires", IEEE Transactions on Knowledge and Data Engineering, vol. 20, No. 2, Feb. 2008, pp. 145-155.

Agrawal et al., "Fast Discovery of Association Rules", Advances in Knowledge Discovery and Data Mining, Menlo Park, AAAI Press, 1996, pp. 307-328.

Appavoo et al., "Enabling Autonomic Behavior in Systems Software With Hot Swapping", IBM Systems Journal, vol. 42, No. 1, 2003, pp. 60-76.

Aronson, Alanr., "MetaMap: Mapping Text to the UMLS Metathesaurus", 2006, 26 pages.

Arpaia et al., "Multi-Agent Remote Predictive Diagnosis of Dangerous Good Transports", Instrumentation and Measurement Technology Conference, Proceedings of the IEEE, May 17-19, 2005, pp. 1685-1690.

(56) References Cited

OTHER PUBLICATIONS

Berchtold et al., "The Mixture Transition Distribution Model for High-Order Markov Chains and Non-Gaussian Time Series", Statistical Science, vol. 17, No. 3, 2002, pp. 328-356.
Berry et al., "Care Coordination for Patients With Complex Health Profiles in Inpatients and Outpatient Settings", Mayo Clinic Proceedings, Available online at: <www.mayoclinicproceedings.org>, 2013, pp. 1-11.
Billari et al., "Timing, Sequencing, and quantum of Life Course Events: A Machine-Learning Approach", European Journal of Population, vol. 22, 2006, pp. 37-65.
Cohen et al., "Integrated Complex Care Coordination for Children With Medical Complexity: A Mixed-Methods Evaluation of Tertiary Care-Community Collaboration", BMC Health Services Research, vol. 12, Article No. 366, Oct. 23, 2012, 23 Pages.
Cook et al., "Making Prophecies with Decision Predicates", ACM 978-1-4503-0490-0/11/01, Jan. 2011, 14 pages.
Deville et al., "Correspondence Analysis with an Extension Towards Nominal Time Series", Journal of Econometrics, vol. 22, 1983, pp. 169-189.
Dijkstra et al., "Measuring the Agreement Between Sequences", Sociological Methods & Research, vol. 24, No. 2, Nov. 1995, pp. 214-231.
Duff, Iains., "Development and history of sparse direct methods", SIAM Conference on Applied Linear Algebra, Available online at: <http://www,numerical.rl.ac.uk/people/isd/isd,html>, Oct. 26-29, 2009, 44 pages.
Dvorak et al., "Football Injuries and Physical Symptoms: A Review of the Literature", The American Journal of Sports Medicine, vol. 28, No. 5, 2000, pp. S3-S9.
Dvorak et al., "Risk Factor Analysis for Injuries in Football Players: Possibilities for a Prevention Program", The American Journal of Sport Medicine, vol. 28, No. 5, 2000, pp. S69-S74.
Han et al., "Frequent Pattern Mining: Current status and future directions.", Data Mining and Knowledge Discovery, vol. 15, 2007, pp. 55-86.
Hawkins et al., "A Prospective Eidemiological Study of Injuries in Four English Professional Football Clubs", Br J Sports Med., vol. 33, 1999, pp. 196-203.
Huyse et al., "Compri-An Instrument to Detect Patients With Complex Care Needs", Psychosomatics, vol. 42, No. 3, May-Jun. 2001, 7 Pages.
John et al., "Neuro-Fuzzy Clustering of Radiographic Tibia Image Data Using Type 2 Fuzzy Sets", Information Sciences, vol. 125, Issues 1-4, 2000, ISSN 0020-0255, Available on Internet at: <https://www.sciencedirect.com/science/article/pii/S0020025500000009>, 2000, pp. 65-82.
Junge et al., "Soccer Injuries: A Review on Incidence and Prevention", Sports Med., vol. 34, 2004, pp. 929-938.
Kang et al., "Mining Based Decision Support Multi-agent System for Personalized e-Healthcare Service", Proceedings of the 2nd KES International conference on Agent and multi-agent systems: technologies and applications, 2008, pp. 733-742.
Kiran et al., "An Improved Multiple Minimum Support Based Approach to Mine Rare Association Rules", Proceedings of the IEEE Symposium on Computational Intelligence and Data Mining, 2009, 8 pages.
Mabry et al., "Clinical Decision Support with IM-Agents and ERMA Multi-agents", Department of Computer Science and Emergency Medicine, 2004, 6 Pages.
Nealon et al., "Agent-Based Applications in Health Care", Applications of Sollware Agent Technology in the Health Care Domain, 2003, pp. 1-17.
Nielsen et al., "Epidemiology and Traumatology of Injuries in Soccer", Am J Sports Med., vol. 17, 1989, pp. 803-807.
Ohno-Machado, Lucila, "Realizing the full potential of electronic health records: the role of natural language processing", Journal of American Medical Information Association, vol. 18 No. 5, Sep. 2011, p. 539.
Othman et al., "Agent Based Preprocessing", International Conference on Intelligent and Advanced Systems 2007, 2007, pp. 219-223.
Prados-Suarez et al., "Contextualized Access to Electronical Health Records in Cardiology", IEEE Transactions on Information Technology in Biomedicine, vol. 16, No. 3, doi: 10.1109/TITB.2011. 2178033., May 2012, pp. 401-412.
Roever, Christian, "Package 'Bayesian Spectral Inference'", r-project. org, Feb. 21, 2013, pp. 1-27.
Sariyar et al., "The RecordLinkage Package: Detecting Errors in Data", The R Journal, vol. 2, No. 2, Dec. 2010, pp. 61-67.
Seibig et al., "Collection of Annotated Data in a Clinical Validation Study for Alarm Algorithms in Intensive Care—A Methodologic Framework", Journal of Critical Care, vol. 25, 2010, pp. 128-135.
Shirabad et al., "Implementing an Integrative Multi-agent Clinical Decision Support System with Open Source Software", Journal of Medical Systems 36, Available online at: <https://doi.org/10.1007/s10916-010-9452-9>, 2012, pp. 123-137.
Ta et al., "Data Descriptor: Columbia Open Health Data, Clinical Concept Prevalence and Co-occurrence from Electronic Health Records", Scientific data, vol. 5, 180273, doi: 10.1038/sdata.2018. 273, Nov. 27, 2018, pp. 1-17.
Townsend, Hilary, "Natural Language Processing and Clinical Outcomes: The Promise and Progress of NLP for Improved Care", Journal of AHIMA, vol. 84, No. 2, Available online at: <https://bok.ahima.org/doc?oid=106198#.XOSgnSgzY2x>, Mar. 2013, 3 pages.
Uhrmacher et al., "Distributed, Parallel Simulation of Multiple, Deliberative Agents", Proceedings of the fourteenth workshop on Parallel and distributed simulation, May 2000, pp. 101-108.
Xue et al., "Fast Query by Example of Environmental Sounds via Robust and Efficient Cluster-based Indexing", 2008 IEEE, International Conference on Acoustics, Speech and Signal Processing, Available online at: <doi: 10.1109/ICASSP.2008.4517532>, 2008, pp. 5-8.
Zaki, Mohammedj., "SPADE: An Efficient Algorithm for Mining Frequent Sequences", Machine Learning, vol. 42, 2001, pp. 31-60.

\* cited by examiner

2/5 SIRS CRITERIA PRESENT – NO ORGAN DYSFUNCTION — 1010

SIRS — 1012
- HR-100BMP
- TEMPERATURE-38.9 C
- RESPIRATIONS-WNL
- GLUCOSE-WNL
- WBC-WNL

ORGAN DYSFUNCTION — 1014
- LACTATE-WNL
- CREATININE-WNL
- PLATELET COUNT-WNL
- BILIRUBIN-WNL
- PTT-WNL
- SYSTOLIC BLOOD PRESSURE-WNL
- MEAN ARTERIAL PRESSURE-WNL
- MENTAL STATUS CHANGE-WNL
- FIO2 RATIO-WNL

ALERT — 1016

"THIS PATIENT HAS MET THE FOLLOWING SIRS CRITERIA (DISPLAY CRITERIA MET). CONTACT THE PHYSICIAN AND CONSIDER ORDERING THE FOLLOWING LABORATORY TESTS".

- LACTATE
- CREATININE
- BILIRUBIN
- PLATELET COUNT
- PTT
- BLOOD CULTURES
- UA

*FIG. 10.*

3/5 SIRS CRITERIA PRESENT – NO ORGAN DYSFUNCTION  1110

1100

SIRS  1112
- HR-100BMP
- TEMPERATURE-38.9 C
- RESPIRATIONS-26BPM
- GLUCOSE-WNL
- WBC-WNL

ORGAN DYSFUNCTION  1114
- LACTATE-WNL
- CREATININE-WNL
- PLATELET COUNT-WNL
- BILIRUBIN-WNL
- PTT-WNL
- SYSTOLIC BLOOD PRESSURE-WNL
- MEAN ARTERIAL PRESSURE-WNL
- MENTAL STATUS CHANGE-WNL
- FIO2 RATIO-WNL

ALERT  1116
"THIS PATIENT HAS MET THE FOLLOWING SIRS CRITERIA (DISPLAY CRITERIA MET). CONTACT THE PHYSICIAN AND CONSIDER ORDERING THE FOLLOWING LABORATORY TESTS".

- LACTATE
- CREATININE
- BILIRUBIN
- PLATELET COUNT
- PTT
- BLOOD CULTURES
- UA

*FIG. 11.*

2/5 SIRS CRITERIA PRESENT – 1 ORGAN DYSFUNCTION — 1210

SIRS — 1212
- HR-100BMP
- TEMPERATURE-38.9 C
- RESPIRATIONS-WNL
- GLUCOSE-WNL
- WBC-WNL

ORGAN DYSFUNCTION — 1214
- LACTATE-3.1MMOL/L
- CREATININE-WNL
- PLATELET COUNT-WNL
- BILIRUBIN-WNL
- PTT-WNL
- SYSTOLIC BLOOD PRESSURE-WNL
- MEAN ARTERIAL PRESSURE-WNL
- MENTAL STATUS CHANGE-WNL
- FIO2 RATIO-WNL

ALERT — 1216
"THIS PATIENT HAS MET THE CRITERIA FOR SEPSIS (DISPLAY SIRS AND ORGAN DYSFUNCTION CRITERIA MET). PLEASE EVALUATE THE PATIENT AND NOTIFY THE PHYSICIAN IMMEDIATELY.

EARLY GOAL DIRECTED THERAPY IS ESSENTIAL FOR THE TREATMENT OF SEPSIS. TIME DEPENDANT INTERVENTION MAY IMPACT PATIENT OUTCOME".

*FIG. 12.*

○ NOTIFICATION MESSAGE

SUBJECT: SEPSIS SCREENING ACUTE CARE
PRIORITY STATUS: HIGH    PRIORITY VALUE: 80
EVENT DATE/TIME: 11/19/2010 1:35:38 PM
MESSAGE CLASS/SUBCLASS: APPLICATION

ALERT

1310 {
NAME: MCKENNA, STEVE
DATE: NOVEMBER 19, 2010 13:35:38 CST
MRN: 00001694
BIRTH DATE: JANUARY 04, 1973
AGE: 37
LOCATION: BASELINE WEST M;  4 NORTH – ICU;  404

THIS PATIENT HAS MET THE CRITERIA FOR SEPSIS. PLEASE EVALUATE PATIENT AND NOTIFY THE PHYSICIAN IMMEDIATELY TO REVIEW THE SEPSIS MANAGEMENT POWERPLAN THAT HAS BEEN SUGGESTED FOR THIS PATIENT.

1312 {
ALERT FOR 2/5 SIRS CRITERIA: "THIS PATIENT HAS MET 2/5 SIRS CRITERIA (DISPLAY CRITERIA MET). CONTACT THE PHYSICIAN AND CONSIDER ORDERING THE FOLLOWING LABORATORY TESTS".
- LACTATE
- CREATININE
- BILIRUBIN
- PLATELET COUNT
- PTT
- BLOOD CULTURES
- UA

EARLY GOAL DIRECTED THERAPY IS ESSENTIAL FOR THE TREATMENT OF SEPSIS. TIME DEPENDANT INTERVENTION MAY IMPACT PATIENT OUTCOME.

1314 {
SIRS CRITERIA
  11/19/10 1328 BLOOD GLUCOSE, CAPILLARY = 125 MG/DL (H) [GREATER THAN 120]
  11/19/10 1328 PERIPHERAL PULSE RATE = 130 BPM (H) [GREATER THAN 90]
  11/19/10 1321 TEMPERATURE ORAL = 39 C (H) [GREATER THAN 38.3]
  11/19/10 1328 RESPIRATORY RATE = 30 BPM (H) [GREATER THAN 20]
ORGAN DYSFUNCTION
  11/19/10 1328 SYSTOLIC BLOOD PRESSURE = 68 MMHG (L) [LESS THAN 90]
  11/19/10 1328 MEAN ARTERIAL PRESSURE, CUFF = 43 MMHG (L) [LESS THAN 65]

*FIG. 13.*

MULTI-SITE CLINICAL DECISION SUPPORT

CROSS REFERENCE TO RELATED APPLICATIONS

This application claims the benefit of U.S. Provisional Application No. 61/391,392, titled "MULTI-SITE CLINICAL DECISION SUPPORT," filed Oct. 8, 2010 and U.S. application Ser. No. 13/269,244, titled "MULTI-SITE CLINICAL DECISION SUPPORT" filed Oct. 7, 2011, which are hereby expressly incorporated by reference in its entirety. This application is related by subject matter to U.S. application Ser. No. 13/269,262, entitled "MULTI-SITE CLINICAL DECISION SUPPORT FOR SEPSIS," filed Oct. 7, 2011, now abandoned, and is herein incorporated by reference in its entirety.

BACKGROUND

The benefits of clinical decision support have been widely demonstrated. Current clinical decision support (CDS) systems operate within the parameters of the information system of a single medical organization. For instance, a patient may have an electronic medical record (EMR) with his or her primary care physician, but this EMR may not be shared with any other medical organizations that are involved with treating the patient, such as an emergency room, an urgent care clinic, a specialist, etc. As such, patient information is typically not shared between facilities, which may impair clinicians in their treatment of patients, as clinicians are unable to see the full scope of the patient's current medical conditions. For example, a patient may have a primary care physician, but may have an urgent medical situation and may go to an urgent care clinic one day, and to the emergency room the next day arising from complications from a procedure performed by a specialist. This scenario is commonplace. Additionally, the case is rare when a patient is seen and treated by multiple clinicians who all use a common medical record system.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In brief and at a high level, this disclosure describes, among other things, methods for surveillance and monitoring of a patient's risk for developing a particular disease or condition. Typically, patients are treated at multiple healthcare facilities, such as hospitals, doctors' offices, urgent care clinics, or the like. These facilities oftentimes are not interrelated and thus do not share medical record systems. Embodiments of the present invention allow for patient information to be received at a monitoring system that monitors, by way of arrays, a patient's risk of developing a particular disease or condition. One exemplary condition is sepsis, which occurs in the presence of an infection with a Systemic Inflammatory Response Syndrome (SIRS) response. This monitoring allows for earlier detection of diseases and conditions so that a patient can be treated earlier, before progression of the disease or condition. Additionally, methods provide clinicians with decision support, such as suggested laboratory tests and other treatment options, based on the patient information.

BRIEF DESCRIPTION OF THE DRAWINGS

The present invention is described in detail below with reference to the attached drawing figures, wherein:

FIGS. 10-12 illustrate exemplary actionable criteria and alerts for a patient being at risk for developing sepsis, in accordance with embodiments of the present invention;

FIG. 13 is an exemplary screen display of an alert after determination that a patient is at risk for developing sepsis, in accordance with an embodiment of the present invention;

DETAILED DESCRIPTION

Figure 1:
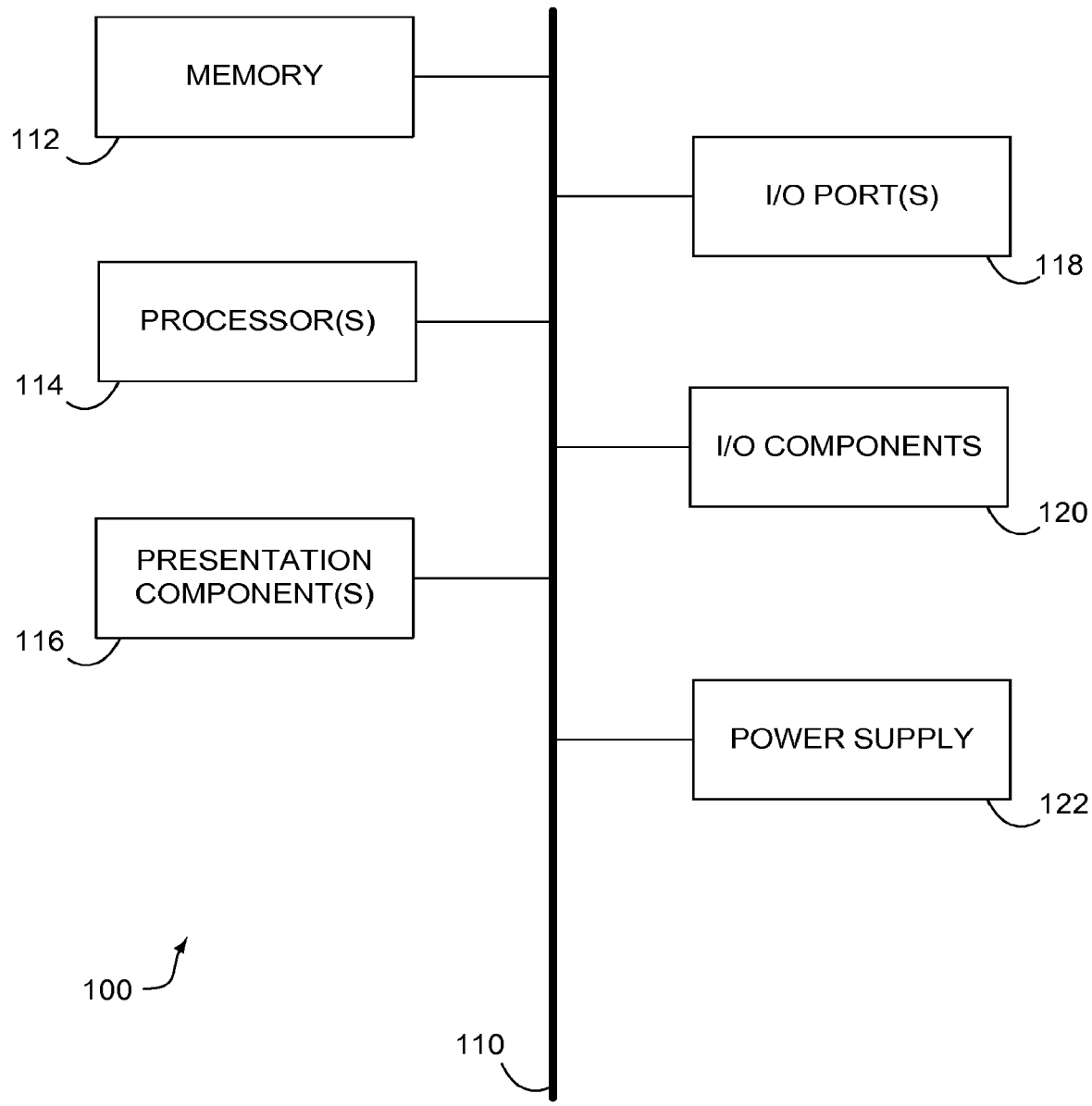
FIG. 1 is a block diagram of an exemplary computing environment suitable for use in implementing embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide decision support capabilities that can benefit patient care across separate venues and organizations. For example, an algorithm in which risk is assessed by evaluating twenty clinical parameters and then escalating to the provider when any two of those parameters qualify for the triggering threshold can be implemented within an institution using a query of all information within that system available at the time that the triggering clinical action occurs. In the multi-site environment, in which each site may only evaluate a subset of the 20 parameters, it is very difficult to accomplish meaningful decision support using a query that is launched at the time of the triggering event.

As such, embodiments of the present invention allow for patient information from multiple, disparate medical organizations having different medical record systems to be used to determine when a patient is at risk for developing a particular disease or condition. When, based on the patient information, it is determined that the patient is at risk, an alert or notification is communicated to one or more of the medical organizations where the patient was treated, the primary care physician of the patient, or the patient. The patient, for instance, may take steps to return to a healthcare facility to be further evaluated. The clinicians, including physicians, nurses, physician assistants, etc., may receive individual alerts or notifications so that they can take action to further evaluate the patient. Similarly, the primary care physician may be alerted so that he or she can take steps to further evaluate the patient. The alerts are sent in near real-time so that time is not wasted, as many diseases or conditions have a higher success rate if the patient is treated in a timely and efficient manner.

In one embodiment of the present invention, a method is provided for enabling multi-site surveillance and decision support for a patient's medical care. The method includes receiving, from a first medical organization, a first set of patient information corresponding to a patient who has received medical treatment at the first medical organization, and determining that an active risk assessment array exists for the patient. The active risk assessment array represents the patient's risk of developing a particular disease or condition. Further, the method includes, for a first node of the active risk assessment array corresponding to the first set of patient information, populating a value of the first node with at least a portion of the first set of patient information. The method additionally includes receiving, from a second medical organization, a second set of patient information. The patient has received medical treatment at the second medical organization, and the first medical organization and the second medical organization maintain separate medical record systems. For a second node of the active risk assessment array corresponding to the second set of patient information, the method includes populating the value of the second node with at least a portion of the second set of patient information. The method also includes determining that actionable criteria for the particular disease or condition have been met based on at least the first and second nodes of the active risk assessment array and providing a notification that the actionable criteria have been met.

In another embodiment of the present invention, one or more computer storage media are provided having computer-executable instructions embodied thereon, that when executed by a computing system having a processor and memory, cause the computing system to perform a method for enabling multi-site surveillance and decision support for a patient's medical care. The method includes receiving a first set of patient information for a patient from a first medical organization, determining that an active risk assessment array does not exist for the patient, and creating the active risk assessment array for the patient for a particular condition or disease for which the patient is to be monitored. Further, the method includes populating values of a first set of nodes of the active risk assessment array with at least a portion of the first set of patient information. The method additionally includes receiving a second set of patient information for the patient from a second medical organization, determining that one or more nodes of the active risk assessment array correspond to at least a portion of the second set of patient information, and populating values of a second set of nodes of the active risk assessment array with the at least the portion of the second set of patient information. Even further, the method includes, based on the values of the first set of nodes and the second set of nodes, determining that the patient has met actionable criteria for being at risk for the particular disease or condition represented by the active risk assessment array. The method also includes notifying one or more of a primary care physician of the patient, the patient, the first medical organization, or the second medical organization that the actionable criteria have been met.

In yet another embodiment of the present invention, one or more computer storage media are provided having computer-executable instructions embodied thereon, that when executed by a computing system having a processor and memory, cause the computing system to perform a method for enabling multi-site surveillance and decision support for a patient's medical care. The method includes receiving a first set of patient information from a first medical organization for a patient and determining whether an active risk assessment array currently exists for the patient. If the active risk assessment array currently exists for the patient, the method includes accessing the active risk assessment array. If, however, the active risk assessment array currently does not exist for the patient, the method includes creating the active risk assessment array for a particular disease or condition for which the patient is to be monitored. Further, the method includes populating values of a first set of nodes of the active risk assessment array with the first set of patient information and receiving a second set of patient information from a second medical organization that maintains a distinct medical record system different from the first medical organization. Also, the method includes associating the first set of patient information with the second set of patient information based on knowledge that they correspond to a common patient and populating the values of a second set of nodes of the active risk assessment array with the second set of patient information. Based on the active risk assessment array, the method includes algorithmically determining that actionable criteria set by the first medical organization indicating that the patient is at risk for developing the particular disease or condition have been met. Additionally, the method includes notifying the first medical organization that the patient is at risk for the particular disease or condition.

Further, in another embodiment of the present invention, a method is provided for detecting sepsis in a patient based on multi-site surveillance. The method includes receiving, from a first medical organization, a first set of patient information corresponding to a patient who has received medical treatment at the first medical organization, and determining that an active risk assessment array exists for the patient, wherein the active risk assessment array represents the patient's risk of developing sepsis. The method also includes, for a first node of the active risk assessment array corresponding to the first set of patient information, populating a value of the first node with at least a portion of the first set of patient information and receiving, from a second medical organization, a second set of patient information. The patient has received medical treatment at the second medical organization, and the first medical organization and the second medical organization maintain separate medical record systems. Additionally, the method includes, for a second node of the active risk assessment array corresponding to at least a portion of the second set of patient information, populating the value of the second node with the at least the portion of the second set of patient information and determining that sepsis-specific actionable criteria have been met based on at least the values of the first node and the second node of the active risk assessment array. Also, the method includes providing a notification that the sepsis-specific actionable criteria have been met.

Additionally, in another embodiment of the present invention, one or more computer storage media are provided having computer-executable instructions embodied thereon, that when executed by a computing system having a processor and memory, cause the computing system to perform a method for detecting sepsis in a patient based on multi-site surveillance. The method includes receiving a first set of patient information for a patient from a first medical organization and based on the first set of patient information, determining that the patient is to be monitored for developing sepsis. The method further includes creating an active risk assessment array for the patient. The active risk assessment array comprises one or more nodes that allow for population of patient information that is specific to sepsis. Further, the method includes populating values of a first set of nodes of the active risk assessment array with at least a portion of the first set of patient information, receiving a second set of patient information for the patient from a second medical organization, and determining that the active risk assessment array that is specific to sepsis is currently active. Additionally, the method includes populating the values of a second set of nodes of the active risk assessment array with at least a portion of the second set of patient information and based on the values of the first set of nodes and the second set of nodes, determining that the patient has met actionable criteria for being at risk for developing sepsis. The method also includes notifying one or more of a primary care physician associated with the patient, the patient, the first medical organization, or the second medical organization that the patient has met the actionable criteria for developing sepsis. The notification is one or more of a flag in the patient's medical record, a message sent to a pager, an email, a text message, a message received at a message center, a telephone call, or a fax.

In yet another embodiment of the present invention, one or more computer storage media are provided having computer-executable instructions embodied thereon, that when executed by a computing system having a processor and memory, cause the computing system to perform a method for detecting sepsis in a patient based on multi-site surveillance. The method includes receiving a first set of patient information from a first medical organization for a patient, determining that, based on the first set of patient information, that the patient is to be monitored for developing sepsis, and determining whether an active risk assessment array corresponding to the patient's risk of developing sepsis currently exists for the patient. If the active risk assessment array currently exists for the patient, the method includes accessing the active risk assessment array, and if the active risk assessment array currently does not exist for the patient, the method includes creating the active risk assessment array corresponding to the patient's risk of developing sepsis. Further, the method includes populating values of a first set of nodes of the active risk assessment array with the first set of patient information and receiving a second set of patient information from a second medical organization that maintains a distinct medical record system different from the first medical organization. The method also includes associating the first set of patient information with the second set of patient information based on knowledge that they correspond to a common patient, populating the values of a second set of nodes of the active risk assessment array with the second set of patient information, and based on the active risk assessment array, algorithmically determining that actionable criteria set by the first medical organization for performing escalation actions has been met. The actionable criteria is met when the patient has a particular high risk for developing sepsis. Further, the method includes, in response to the actionable criteria being met, performing the escalation actions, wherein the escalation actions comprise notifying the first medical organization that the actionable criteria has been met for the patient.

Embodiments of the technology may take the form of, among other things: a method, system, or set of instructions embodied on one or more computer-readable media. Computer-readable media include both volatile and nonvolatile media, removable and nonremovable media, and contemplate media readable by a database, a switch, and various other network devices. By way of example, and not limitation, computer-readable media comprise media implemented in any method or technology for storing information, such as computer storage media. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

An exemplary operating environment suitable for implementing embodiments of the present invention is described below. Referring to the drawings in general, and initially to FIG. 1 in particular, an exemplary operating environment for implementing embodiments of the present invention is shown and designated generally as computing device 100. Computing device 100 is but one example of a suitable computing environment and is not intended to suggest any limitation as to the scope of use or functionality of embodiments of the present invention. Neither should the computing environment 100 be interpreted as having any dependency or requirement relating to any one or combination of components illustrated.

Embodiments of the present invention may be described in the general context of computer code or machine-useable instructions, including computer-executable instructions such as program components, being executed by a computer or other machine, such as a personal data assistant or other handheld device. Generally, program components including routines, programs, objects, components, data structures, and the like refer to code that performs particular tasks, or implements particular abstract data types. Embodiments of the present invention may be practiced in a variety of system configurations, including handheld devices, consumer electronics, general-purpose computers, specialty computing devices, etc. Embodiments of the invention may also be practiced in distributed computing environments where tasks are performed by remote-processing devices that are linked through a communications network.

With continued reference to FIG. 1, computing device 100 includes a bus 110 that directly or indirectly couples the following devices: memory 112, one or more processors 114, one or more presentation components 116, input/output (I/O) ports 118, I/O components 120, and an illustrative power supply 122. Bus 110 represents what may be one or more buses (such as an address bus, data bus, or combination thereof). Although the various blocks of FIG. 1 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventors hereof recognize that such is the nature of the art and reiterate that the diagram of FIG. 1 is merely illustrative of an exemplary computing device that can be used in connection with one or more embodiments of the present invention. Distinction is not made between such categories as "workstation," "server," "laptop," "handheld device," etc., as all are contemplated within the scope of FIG. 1 and reference to "computer" or "computing device."

Memory 112 includes computer storage media in the form of volatile and/or nonvolatile memory. The memory may be removable, nonremovable, or a combination thereof. Exemplary hardware devices include solid-state memory, hard drives, optical-disc drives, etc. Computing device 100 includes one or more processors that read data from various entities such as memory 112 or I/O components 120. Presentation component(s) 116 present data indications to a user or other device. Exemplary presentation components include a display device, speaker, printing component, vibrating component, etc. I/O ports 118 allow computing device 100 to be logically coupled to other devices including I/O components 120, some of which may be built-in. Illustrative components include a microphone, joystick, game pad, satellite dish, scanner, printer, wireless device, etc.

Figure 2:
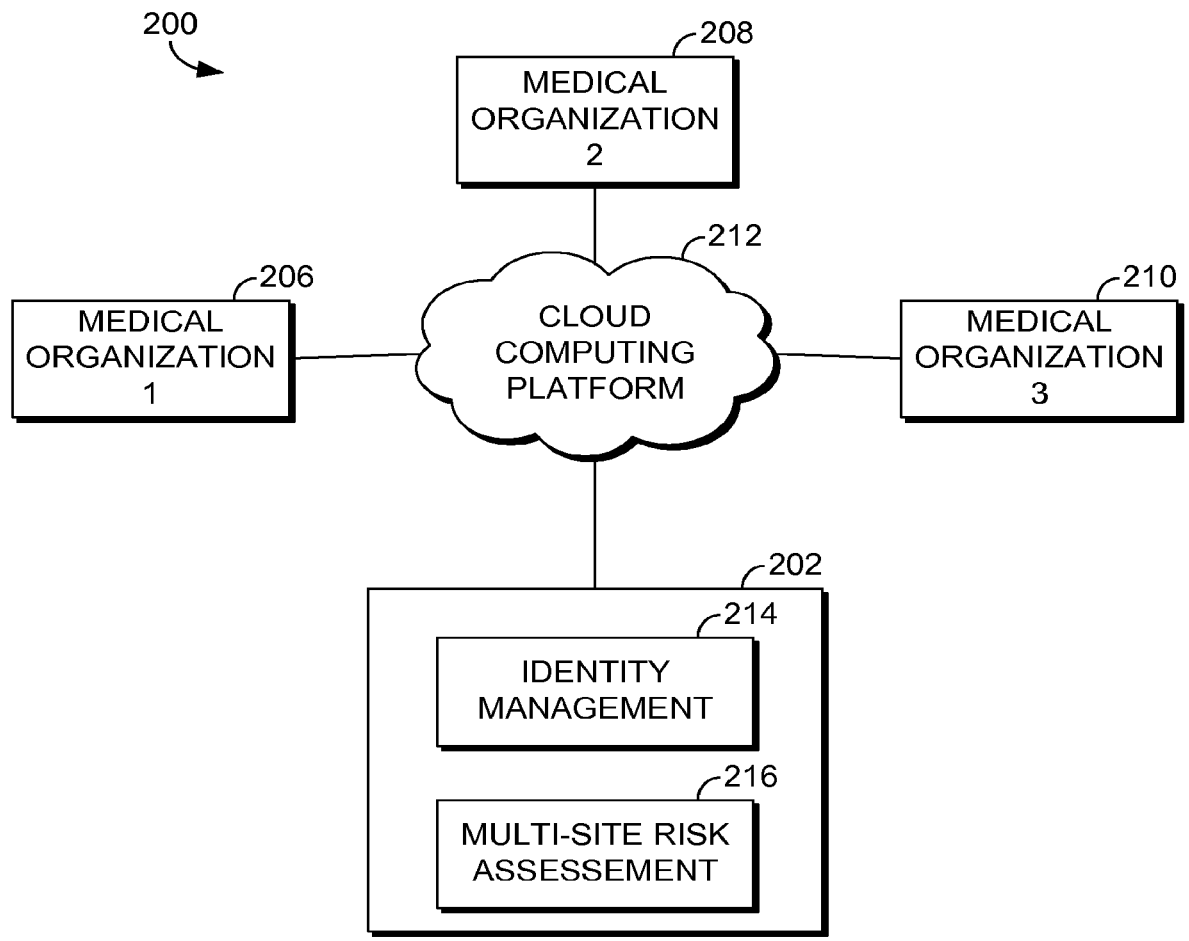
FIG. 2 is a block diagram showing an exemplary architecture for facilitating multi-site clinical decision support in accordance an embodiment of the present invention.

Turning now to FIG. 2, a block diagram 200 is illustrated, in accordance with an embodiment of the present invention, showing an exemplary cloud computing platform 212 for use by multi-site decision support manager 202. It will be understood and appreciated that the cloud computing platform 212 shown in FIG. 2 is merely an example of one suitable computing system environment and is not intended to suggest any limitation as to the scope of use or functionality of embodiments of the present invention. For instance, the cloud computing platform 212 may be a public cloud, a private cloud, or a dedicated cloud. Neither should the cloud computing platform 212 be interpreted as having any dependency or requirement related to any single component or combination of components illustrated therein. Further, although the various blocks of FIG. 2 are shown with lines for the sake of clarity, in reality, delineating various components is not so clear, and metaphorically, the lines would more accurately be grey and fuzzy. In addition, any number of physical machines, virtual machines, data centers, endpoints, or combinations thereof may be employed to achieve the desired functionality within the scope of embodiments of the present invention. As mentioned, cloud computing platform 212 comprises a cloud-computing network, which is known in the art as "the cloud."

The cloud computing platform 212 includes a data center configured to host and support the operation of the manager 202. The manager 202 refers to any software, or portions of software, that runs on top of, or accesses storage locations within, the platform 212. It will be appreciated that cloud computing platform 212 may include multiple computing devices such as computing devices or portions of computing devices 100 shown in FIG. 1. Cloud computing platform 212 may include virtual machines, such as software, application, operating system, or program that is executed by a processing unit to underlie the functionality of multi-site decision support manager 202. Further, the virtual machines may include processing capacity, storage locations, and other assets to support the multi-site decision support manager 202. In one instance, the computing devices of separate medical organizations, such as medical organizations 206, 208, and 210, host and support the operations of the multi-site data manager, while simultaneously hosting applications.

In one aspect, the cloud computing platform 212 can communicate internally through connections dynamically made between the virtual machines and computing devices and externally through a physical network topology to resources of a remote network such as with medical organizations 206, 208, and 210. By way of example, the connections may include, without limitation, one or more local area networks (LANs) and/or wide area networks (WANs). Such networking environments are commonplace in offices, enterprise-wide computer networks, intranets, and the Internet. Accordingly, the network is not further described herein.

As shown in FIG. 2, the multi-site decision support manager 202 is capable of communicating with a number of different entities or medical organizations, such as a hospital 206, a physician's office 208, and urgent care clinic 210, for example, for the collection of patient information from a number of individual entities. Patient information collected from different entities may include, but is not limited to, information that describes various aspects of the patient state, including patient vitals, lab results, medication orders, diagnosis codes, condition codes, clinical orders, indexed values from clinical notes or other text documents, patient demographic information, patient history, patient images, and a variety of other patient information.

It should be noted that the medical organizations shown as communicating with multi-site decision support manager 202 in FIG. 2 are provided by way of example only and are not intended to limit the scope of the present invention in any way. Each medical organization may have one or more computing devices such as computing device 100 of FIG. 1, for communicating with the decision support manager 202. It will be appreciated that each medical organization is an organization for treating patients such as a hospital, urgent care clinic, physician's office, emergency department, and the like. Each medical organization maintains its own enterprise healthcare system and each organization is not directly connected with one another such that separate medical record systems are utilized by each medical organization. The medical organizations send information to the cloud computing platform 212 and not typically directly between one another. In addition, communication between the manager 202 and the various medical organizations may be via one or more networks, which may comprise one or more wide area networks (WANs) and one or more local area networks (LANs), as well as one or more public networks, such as the Internet, and one or more private networks.

Further, medical organizations may be able to access the manager 202 in a variety of ways within the scope of the present invention. For example, in some embodiments, a medical organization may have a native clinical computing system, which may be able to communicate with the manager 202. In other embodiments, a client application associated with the manager 202 may reside or partially reside on one or more of the medical organization's computing devices facilitating communication with manager 202. In further embodiments, communication may simply be a web-based communication, using, for example, a web browser to communicate to the manager 202 via the Internet. Any and all such variations are contemplated to be within the scope of embodiments of the present invention.

Manager 202 is available in the cloud computing platform 212 in a manner that enables the cross-venue recognition of a patient through the use of a patient identity management component 214 such as an Electronic Master Person Index (EMPI). Patient identity management component 214 allows manager 202 to match data for the same patient that originates with different medical organizations. A processing element of manager 202 receives and monitors new information for an individual patient (from Continuity of Care Documentation (CCD), extracted information HL7 messages) that is sent to the cloud platform 212 to determine whether or not it is appropriate to open a multi-site risk assessment array 216 for an individual patient for a particular condition.

Exemplary conditions for which an array may be opened for a patient include, but are not limited to, sepsis, infection risk (both community and hospital acquired), blood management and anemia care, shock, Venous thromboembolism (VTE), heart failure, asthma, renal failure/dialysis, wound care, compliance, immunizations, injury patterns, COPD care, controlled substance manipulation, emergent surgical evaluation, travel medicine, dependent care (pediatric and elderly), and system abuse. A sentinel or triggering event may be identified by manager 202 based on information sent to cloud platform 212 by one or more medical organizations 206, 208, and 210. If a triggering occurs, a transient array for the patient is created. A state-based array is created that persists or remains active in the cloud platform 212 over a defined period of time, which may be determined based on the nature of clinical utility of the condition or disease represented by the array. An audit trail of time of patient information, medical organization sending patient information, and other information is created and maintained. A persistent array 216 offers performance advantage because the information from multiple medical organizations remains together on demand to support a specific decision support objective versus having to perform a query of one medical organization's information at the time the information is needed. In one embodiment, agents may be used to update the array 216, read the array, and otherwise access the array information that is stored in a database. If implemented, inclusion or exclusion nodes can also be populated at this time.

Manager 202 builds a multi-site risk assessment array 216 for an individual patient. Multi-site risk assessment array 216 includes one or more state "nodes" or compartments for the individual patient. Each node in the array 216 represents a distinct parameter for a particular condition or patient information. Array 216 includes a defined period of persistence based on the nature of the clinical utility of the particular condition. For example, an array for sepsis for the patient may last 48 hours while an array for controlled substance manipulation for the patient may last years.

One or more nodes of the array 216 may be supplemented with additional nodes that are used to influence exclusion or inclusion logic (for example, if glucose levels are state node, it may be necessary to also define an exclusion node that is flipped for diabetic patients, indicating to the evaluation agent that the glucose node should be ignored). In addition, a single patient may have multiple arrays open at the same time. Based on the persistence criteria for each array, the number of active arrays for a single patient may be in flux.

It is likely that not all nodes in the system will be populated by each medical organization due to limitations in the electronic health record implementations at each medical organization. For example, if there are 20 nodes, medical organization 1 may only populate nodes 1-5, 7, 12, and 18-20, while medical organization 2 populates nodes 1-6, 8, 14 and 17-20. Collectively medical organizations 1 and 2 would have populated nodes 1-8, 12, 14 and 17-20, creating a more comprehensive view of the patient status than either site was individually able to generate. This allows for gaps in patient information to be filled in across sites and over time.

Population of the status of each node of array 216 is determined from the patient information received for the individual patient based on logic applied to the information. The logic used may include, but is not limited to, binary findings such as: 1) presence or absence of a clinical finding for the individual patient; 2) presence or absence of a medication for the individual patient; 3) presence or absence of a diagnosis code for the patient; and 4) presence or absence of a social history indicator for the patient. The logic applied to the patient information may also be range-based findings such as: 1) a vital sign for an individual patient being above or below a threshold; 2) a lab result for a patient that is greater than or less than a threshold value; 3) whether a condition of a patient has persisted for longer than an indicated duration; and 4) whether a condition for a patient disappears sooner than an indicated duration.

The status or visual indicator of each node in array 216 may also vary based on the patient information. Visual indicators of each node are shown in more detail with respect to FIGS. 4-8 and discussed in more detail below. The node status can be: 1) binary (on or off); 2) ranged, such as a sliding scale (e.g., the higher the patient's temperature the darker the color of the node); 3) based on a numerical representation (e.g., number of the patient's temperature); or 4) coded.

A manager 202 monitors the active arrays 216 to determine when the actionable criteria for arrays 216 have been met, and if so, triggers escalation logic. The monitoring can be based on, but not limited to: 1) the number of nodes in an on state; and 2) a calculated value if nodes use numeric state. For example, if there are five nodes, each of which can have a value of 0-3, the escalation logic could be triggered by a total value of five or more. The monitoring can be based on a combination of "on" and calculated values (e.g., three nodes in a "warning" status=equivalent of one node in an active status). Manager 206 can escalate based on escalation logic implemented in a number of manners. These include but are not limited to active escalation methods including: 1) sending an alert to the primary provider on record for that patient; 2) sending an alert to all providers with documented patient contact during the window of activity for the matrix; and 3) sending an alert to the patient encouraging the patient to take further action by returning to the patient's provider or going to the emergency department. Reactive escalation may include modifying the system behavior due to the status of the patient's array, based upon the next patient event (such as admission, new order, opening patient's chart). Modifications of system behavior can include: 1) visually flagging the patient in the system; 2) proactively assembling previous records for immediate review at time of next admission; and 3) recommending a care plan to the provider currently interacting with the system.

Upon conclusion of the persistence period defined for the specific array 216, the status of the array is changed to "closed." This will retain the information for audit trail purposes, while preventing it from inappropriately interjecting into subsequent episodes of care.

Figure 3:
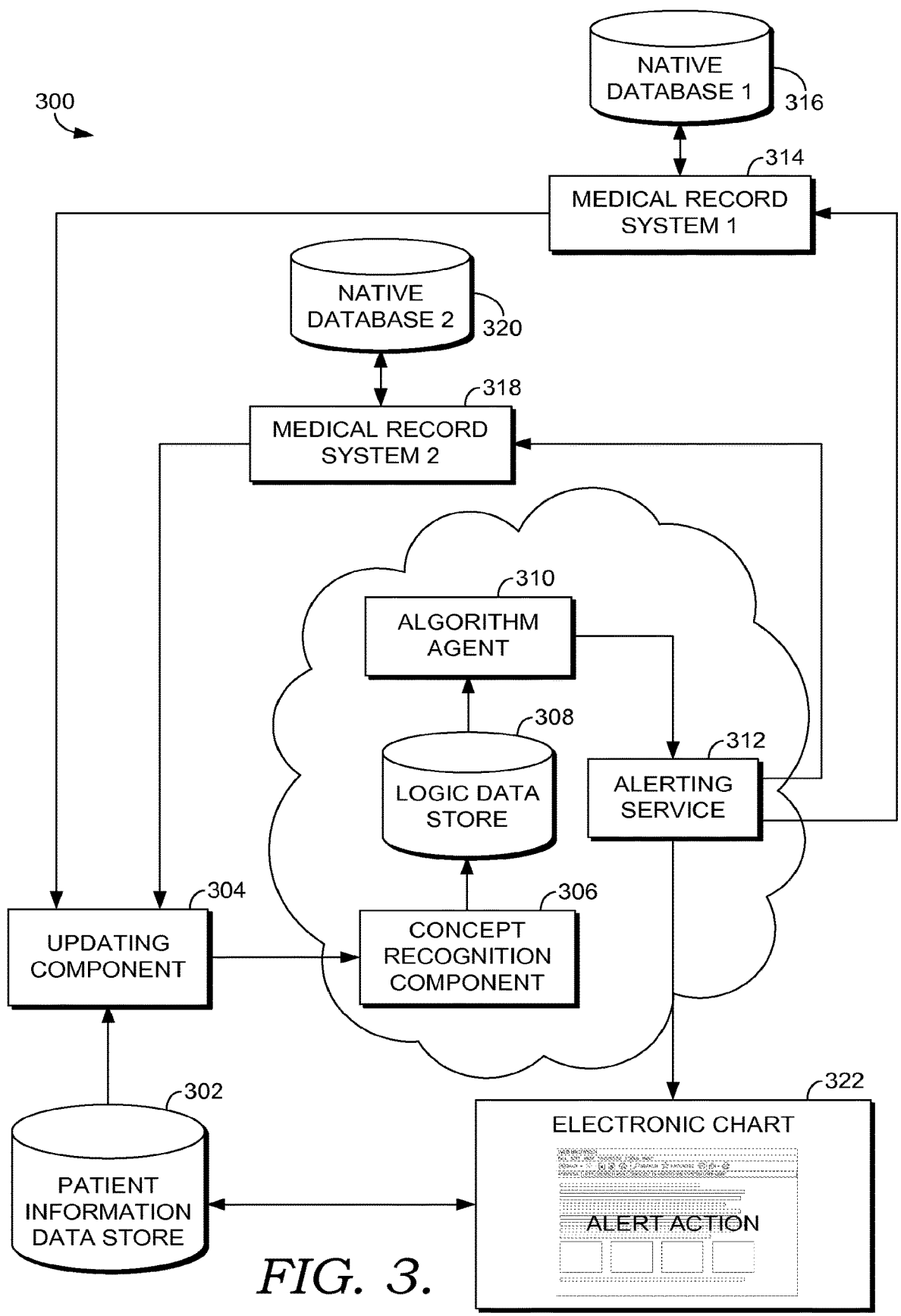
FIG. 3 is a block diagram of an exemplary system for enabling multi-site surveillance and decision support for a patient's medical care, in accordance with an embodiment of the present invention.
Figure 4:
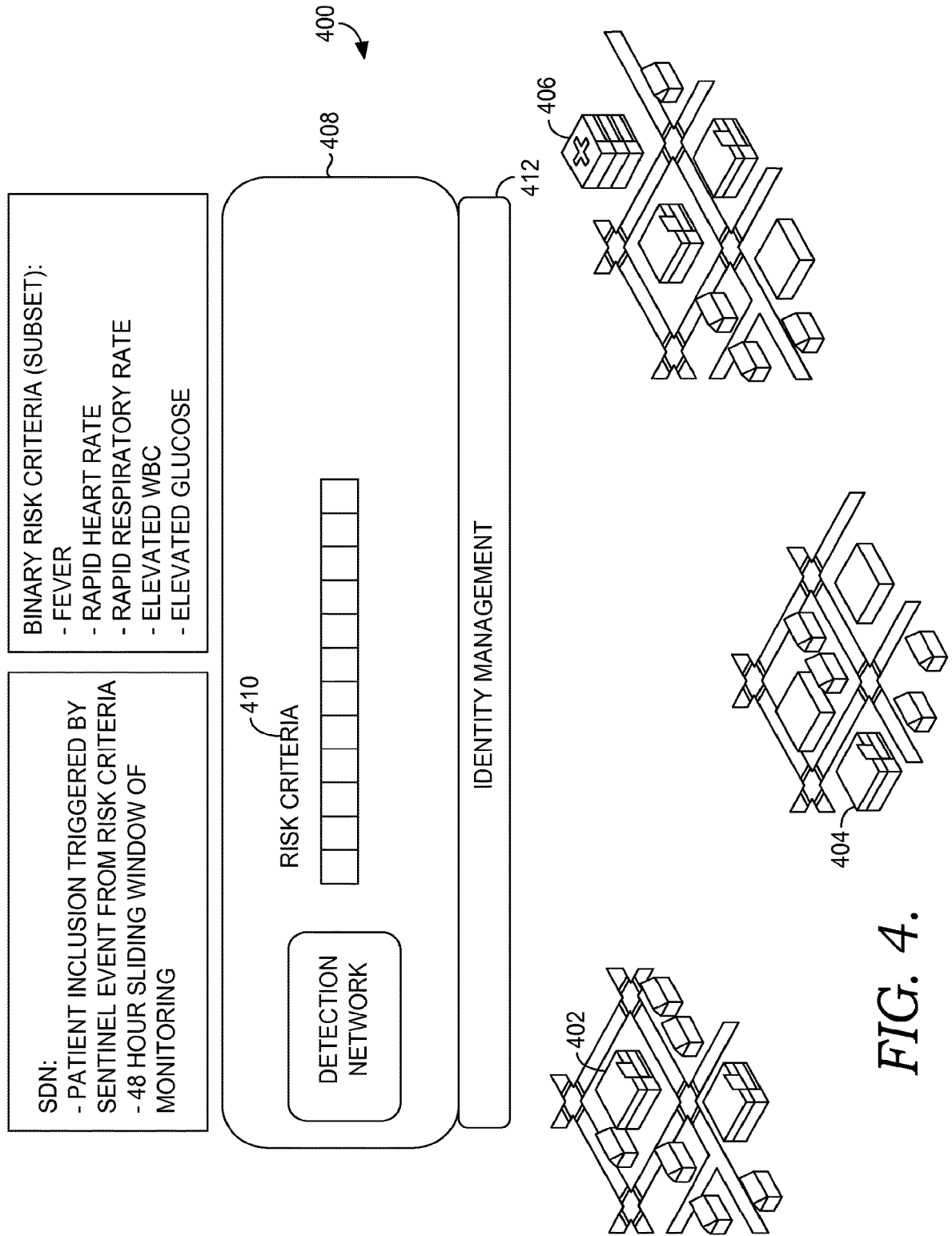
FIGS. 4-8 are diagrams showing multi-site decision support, in accordance with embodiments of the present invention.

Turning now to FIG. 3, a block diagram of an exemplary system 300 is shown for enabling multi-site surveillance and decision support for a patient's medical care, in accordance with an embodiment of the present invention. Initially, a patient information data store 302 is illustrated that stores information including patient records, such as electronic medical records (EMR) that can be accessed by various applications. For instance, a particular patient's EMR may be accessed by one or more providers associated with different medical organizations. Further, a patient's EMR may not be accessed by a particular provider at a particular medical organization, but may be populated by patient information received from that provider at the medical organization. For example, multiple medical organizations, including hospitals, clinics, doctors' offices, etc., may treat the same patient at some point in time, but may not share a common medical record system, and thus may not all have access to the patient's EMR. Instead, these medical organization's may send patient information to a location that stores the patient's EMR so that this information can be populated into the EMR. This patient information may also be monitored and used to determine whether the patient is at risk of developing a particular disease or condition.

The patient information can be returned by one of several methods. For instance, the updating component 304, in one embodiment, acts as a crawler and actually reaches into another medical organization's medial record system to pull relevant information for a particular patient who is being monitored or who may be monitored in the future for being at risk for a particular disease or condition. The updating component 304, similarly, may query the medical organizations medical record system to obtain this patient information. Using this method, the crawler may include a program or application that tells it exactly what type of information to retrieve. Alternatively, the updating component 304 may not have the capability or permission to crawl for patient information, but may receive patient information such that it is the responsibility of the medical organization treating the patient to send the patient information to the updating component 304. Using either method, the updating component 304 eventually receives patient information. The concept recognition component 306 is generally responsible for reconciling terms used by the various medical organizations. For instance, if a first medical organization calls a white blood cell count test WBC and a second medical organization calls the same test WC, the concept recognition component 306 would have this information stored to determine that both terms are referring to the same test. In some instances, the concept recognition component 306 reconciles the test results themselves, such as if two different medical organizations use a different measuring system.

The logic data store 308 stores logic that is used to determine when a patient is at risk for a particular disease or condition and when it is the appropriate time to alert one or more medical organizations, the patient, the primary care provider, etc., that the patient is at risk based on the patient information received from the multiple medical organizations. In one embodiment, the logic data store stores arrays that will be discussed in more detail in references to FIGS. 4-8 below. Arrays, as used herein, are a management system for monitoring the symptoms that a user has in reference to a particular disease or condition. This information, together, is called an array. Some boxes of an array may have patient information and some may not, indicating that patient information corresponding to the blank boxes has not yet been received from the medical organizations. It should be noted that arrays have a duration of time in which they remain active. This duration of time is dependent, at least in part, on the disease or condition that is being monitored in relation to the patient. For instance, an array for monitoring a patient's risk of sepsis may be active for 24-48 hours, or even up to 72 hours. An array for substance abuse, on the other hand, may be active for several years. The duration of an array may be nonmodifiable, or may be modifiable by a medical organization, the primary care physician, or the system that monitors the patient's risk for a particular disease or condition. The concept recognition component 306 may communicate various patient identifying information to the logic data store 308, including an identification of the patient.

The algorithm agent 310 is responsible for executing algorithms or logic, such as the logic stored in the logic data store 308. These algorithms or logic determine when, based on an array, the patient is at risk for developing a particular disease or condition. Exemplary logic will be further discussed in relation to FIGS. 9A and 9B. The algorithm agent 310 may additionally be responsible for updating the logic based on results of patient monitoring. For instance, algorithm agent 310 may include a multi-agent system that may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities, and choices that communicate via declarative messaging and use abstractions to allow for future adaptations and flexibility. An agent has its own thread of control, which promotes the concept of autonomy. For example, the multi-agent system may have knowledge as to whether patients for which alerts are sent are actually diagnosed with the disease or condition for which they are being monitored. If the percentage is low or otherwise unacceptable as to the patients being diagnosed, the criteria for being at risk for that disease or condition may be altered such that alerts and notifications are sent when a different set of criteria is met. Further, the individual medical organizations may have individual criteria that they use to determine when a patient is at risk, and thus when it would like to receive an alert from the monitoring system. The algorithm agent 310 may monitor this information to determine when it is appropriate to alert, notify, etc., one or more medical organizations or other parties involved in the medical care of the patient. For instance, each provider with document patient contact during a period of time that the active risk assessment array has been active may be notified, in one embodiment.

The alerting service 312 receives input from the algorithm agent 310 as to when and who to alert. In an alternative embodiment, the alerting service 312 is responsible for using inputs from the algorithm agent 310 to determine when and who to alert. The alerting service 312 may comprise one or more rules that allow the alerting service 312 how to determine when to communicate an alert, notification, etc. In one embodiment, each medical organization that has provided patient information to the monitoring system receives an alert when the criteria are met for the patient being at risk for a particular disease or condition. Further, the patient may be alerted via a text message, a telephone call, a letter, an e-mail, etc., so that the patient can initiate a follow-up appointment with the primary care physician or another provider. Even further, the primary care physician, while he or she may not have provided any patient information that was used in the array to determine that the patient is at risk for a particular disease or condition, may be alerted. In some embodiments, the notification or alert is recorded in an electronic chart 322 corresponding to the patient, such as an EMR so that it can be used for future reference by other clinicians.

While in some embodiments, the monitoring system establishes the criteria for determining whether a patient is at risk for a particular disease or condition, in another embodiment, each medical organization may use different criteria for determining whether a patient is at risk for a particular disease or condition. For instance, a first medical organization may use a heart rate criteria of above 95 beats per minute (bpm) for a patient being at risk for developing sepsis. A second medical organization may use a heart rate criteria of above 98 bpm for a patient being at risk for developing sepsis. When a patient's heart rate is at 96 bpm and other criteria are met for being at risk for developing sepsis, the first medical organization may receive an alert, but the second medical organization may not receive an alert, in some embodiments. In these embodiments, the second medical organization may receive a notification indicating that the first medical organization received an alert based on its criteria for sepsis. This may prompt the second medical organization to take a closer look at the patient's medical information to determine whether it needs to take action. While there are many different ways of implementing an alerting service 312, the previous examples are provided as illustrations as to how the alerts and notifications may operate and do not limit embodiments of the present invention. Other scenarios not specifically mentioned here are contemplated to be within the scope of the present invention.

As shown, alerting service 312 can alert the medical organizations by communicating an alert to the medical record system used by each medical organization. For instance, the first medical organization may utilize medical record system 1 (item 314), which has a native database 1 (item 316) that stores patient information including EMRs for each of the medical organizations with which it operates. The alert may be communicated to medical record system 1 (item 314), and then the alert is sent to the particular medical organization or clinician within that medical organization. Similarly, the alert may be communicated to medical record system 2 (item 318), which has a native database 2 (item 320) for storing patient information including EMRs for each of the medical organizations with which it operates. The alert may appear on the patient's EMR, or may be sent directly to the clinician responsible for treating the patient. As shown in FIG. 3, the medical record systems send patient information to the updating component 304. This patient information is the patient information used to populate the arrays to determine whether a patient is at risk for a particular disease or condition. While the patient information comes from individual medical organizations, each medical organization may utilize a particular medical record system, and thus when the practitioner enters patient information into the patient's EMR at the medical organization (e.g., hospital, urgent care, doctor's office), the patient information is sent to the medical record system where it is stored. The alert sent from the alerting service 312 may take many forms, including, for exemplary purposes only and not limitation, an email, text message, telephone call, pager message, fax, or the like. Even further, the alert may comprise a recommended care plan for the provider based on the patient information received.

As shown in FIG. 3, the concept recognition component 306, the logic data store 308, the algorithm agent 310, and the alerting service 312 are in the cloud. As mentioned, cloud computing generally refers to a way for on-demand network access to a shared pool of configurable computing resources, including, for instance, networks, servers, storage, applications, services. As such, the components listed above in the cloud are accessible by way of the Internet. While these components are shown in the cloud, other components may also be in the cloud, although not shown in FIG. 3.

Figure 5:
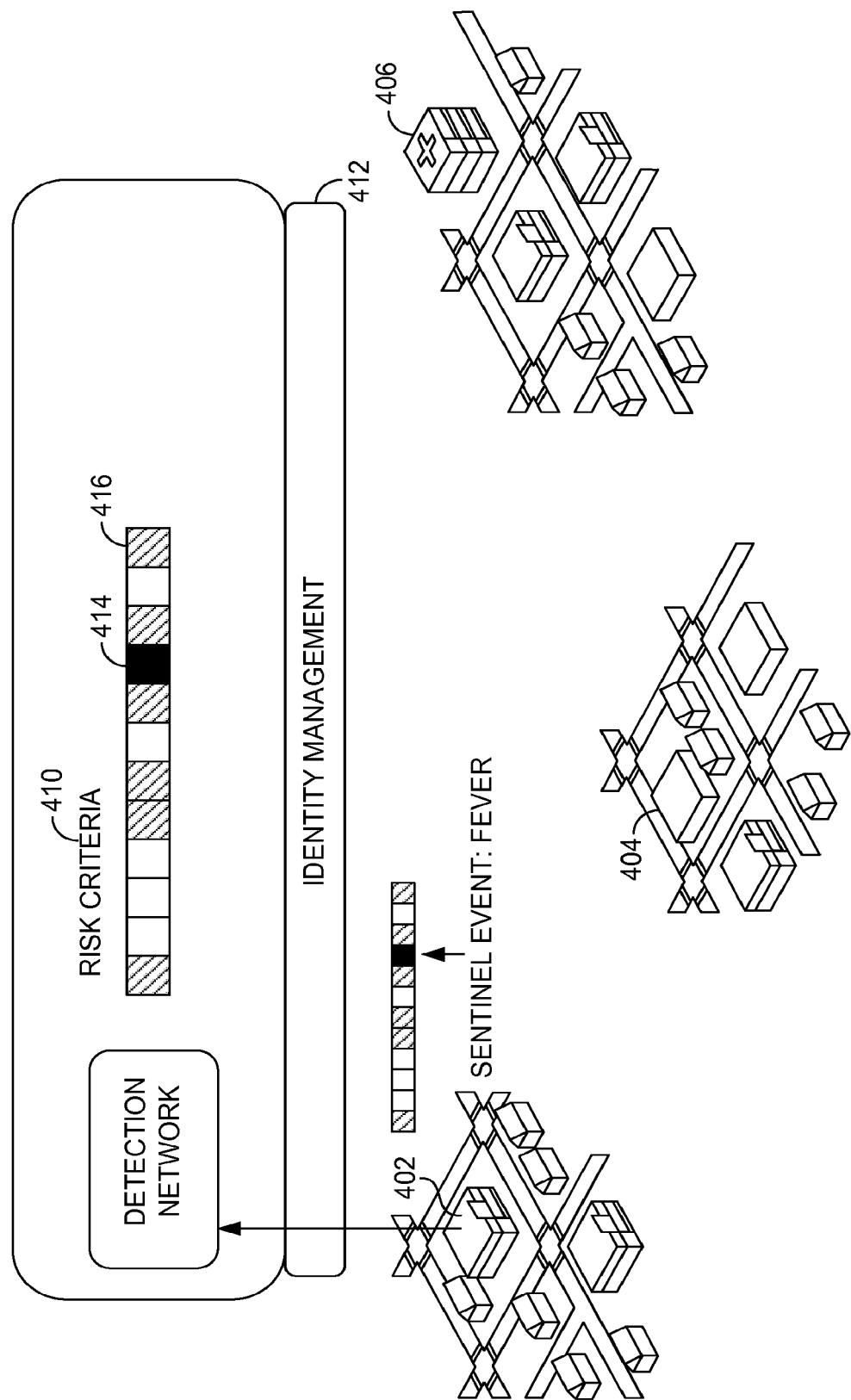

Referring now to FIGS. 4-8, an example 400 of monitoring patient data from multiple organizations for decision support is shown. Three organizations, a physician's office 402, urgent care clinic 404 and emergency room of a hospital 406, are sending patient information to manager 408 (also manager 202 of FIG. 2). An identity management component 412 (such as 214 of FIG. 2) identifies the patient information so that it can be correlated with information for the same patient from other organizations. In this example, there are multiple risk criteria for a sepsis array including: fever, rapid heart rate, rapid respiratory rate, elevated white blood cells, and elevated glucose. The sepsis array is triggered by satisfaction of one of the risk criteria and is set to persist in a cloud computing environment for 48 hours. With reference to FIG. 5, the sentinel event of a fever 414 occurs and is reported by the patient's physician's office 402 to the manager 408. The elevated fever 414 satisfies one of the risk criteria and a sepsis array 410 is opened for the patient. Gray boxes, such as box 416, indicate boxes or nodes that have patient information that has been received from one or more of the medical organizations and has been populated into the array.

As shown in FIG. 5, risk criteria 410 may be dark boxes that are satisfied risk criteria, such as box 414, gray boxes that are criteria reported by that particular organization (in this case the physician's office), such as box 416, and white boxes represent criteria that are not reported by the particular organization. It will be appreciated that satisfied criteria, reported but not satisfied criteria and not reported criteria may be identified in any variety of manners including by colors (red, green, and white) or other visual representations.

Figure 6:
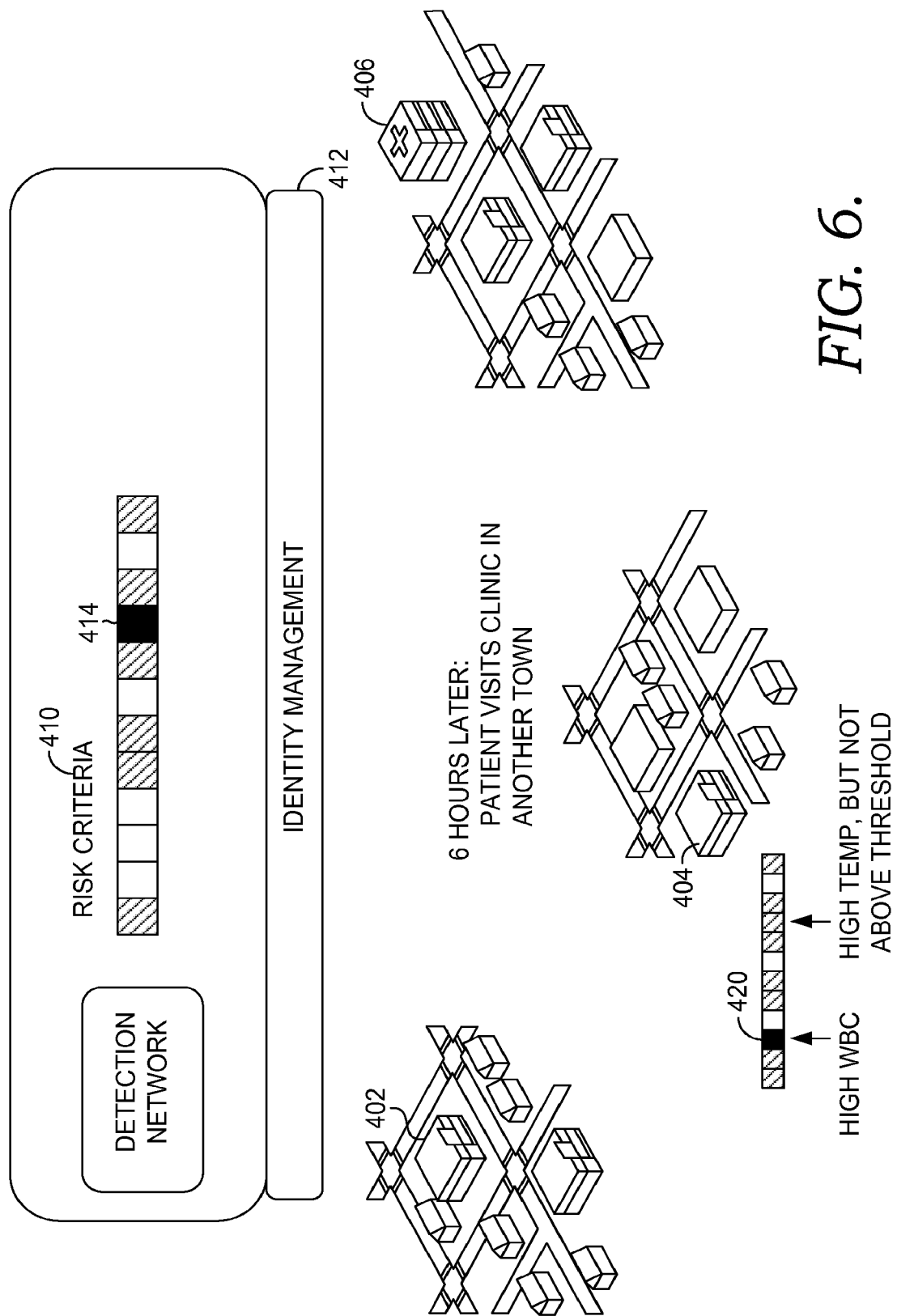
Figure 7:
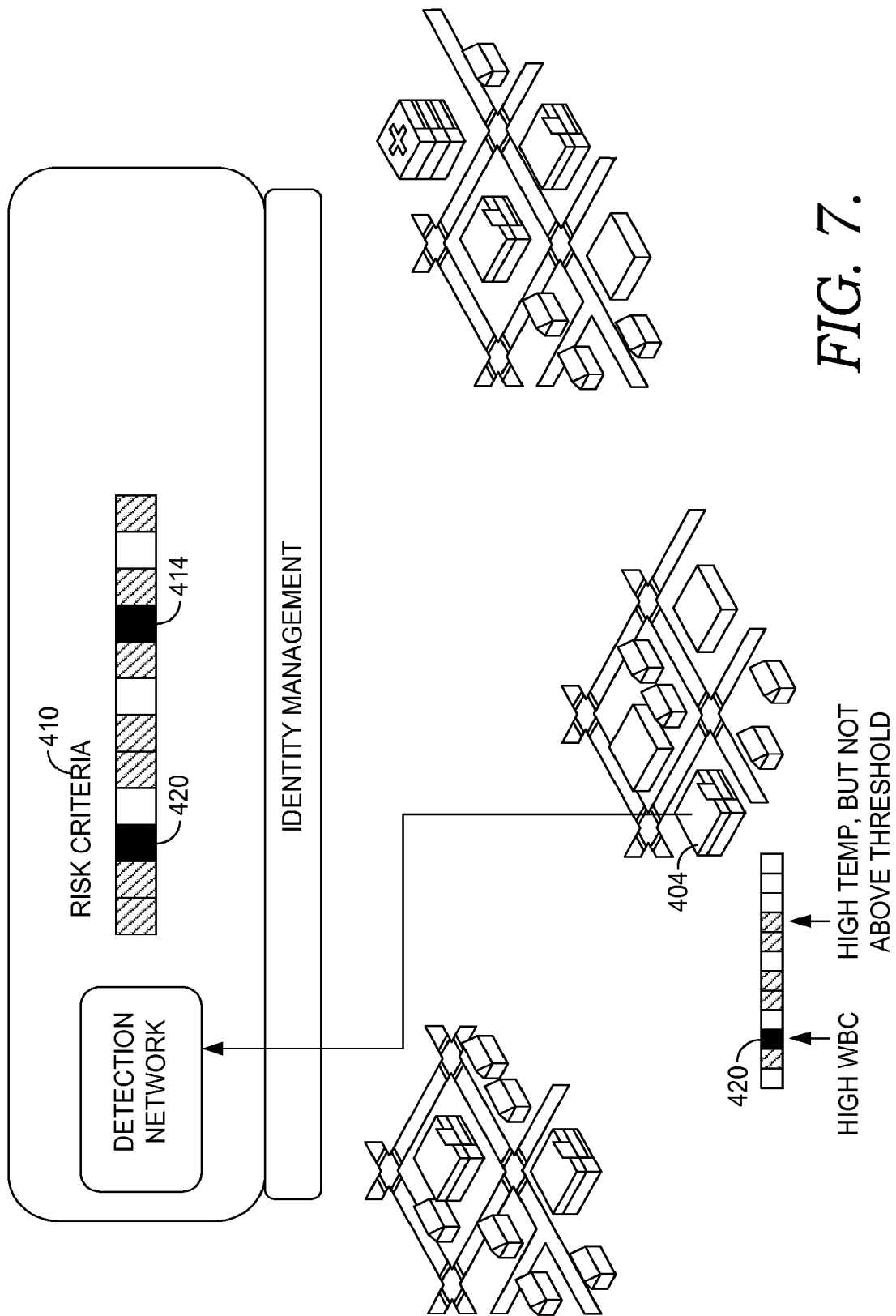

With reference to FIGS. 6 and 7, six hours later while visiting urgent care clinic 404 across town, which is separate from and not connected to the physician's office 402, the urgent care clinic 404 sends patient information to the manager 408 indicating that the patient has a high white blood cell count 420. This information is populated by the manager 408 into the sepsis array 410 already existing for the patient based on the patient's previous visit to physician's office 402.

Figure 8:
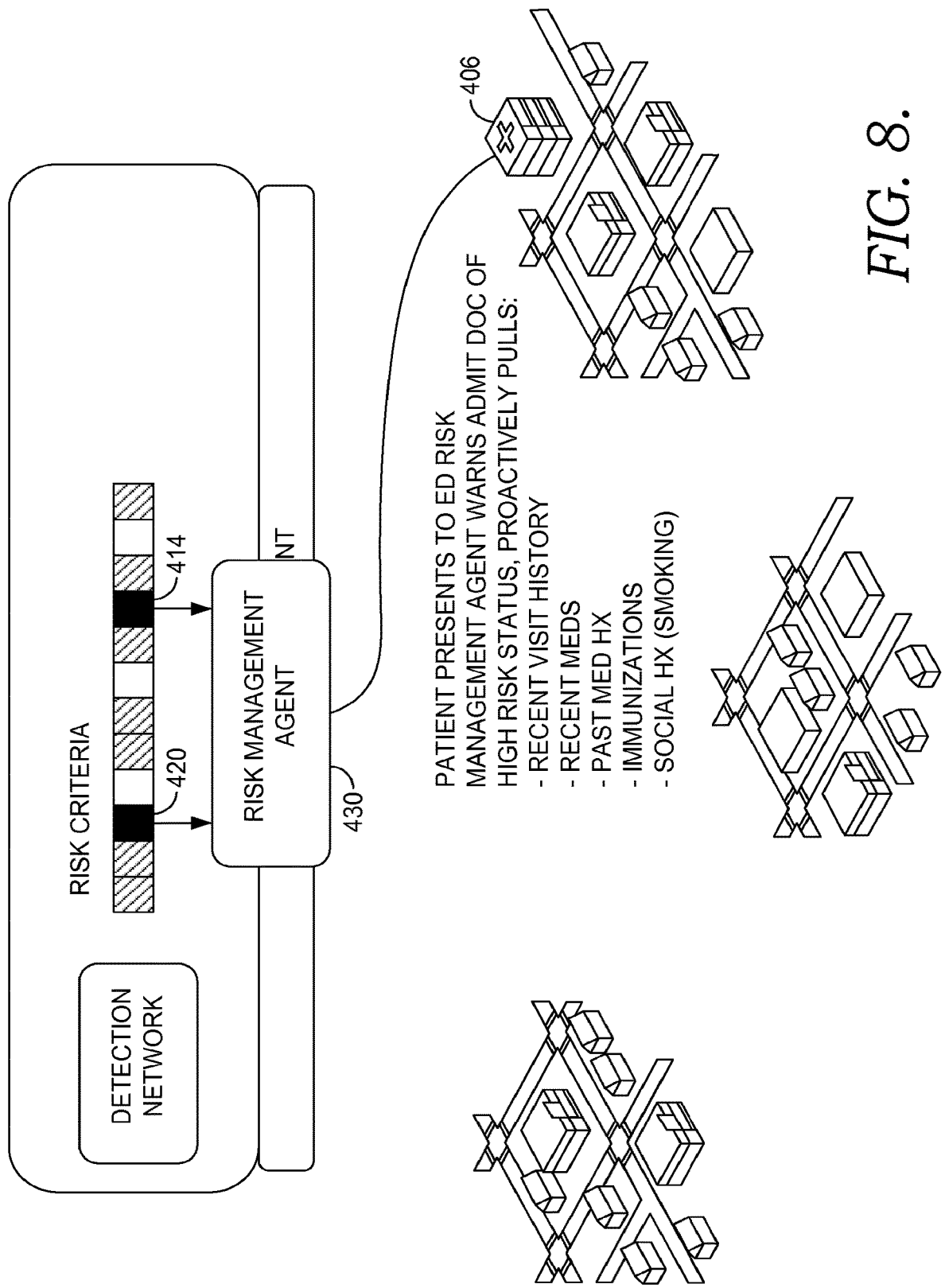

With reference to FIG. 8, when the patient later presents to the emergency department 406 at the local hospital, the risk management agent 430 of manager 408 warns the admitting emergency doctor of the patient's high-risk status for sepsis and proactively pulls and provides to the admitting emergency doctor the recent visit history for that same patient, a recent medication list, past medical history, immunization, and social history for the patient. Thus, the admitting emergency doctor is provided with an immediate picture of the patient's health over the last 48 hours based on the persistent state-based array that has been maintained by the manager 408 for the patient so that the treating clinician can quickly identify issues and quickly treat the patient if needed.

Figure 9A:
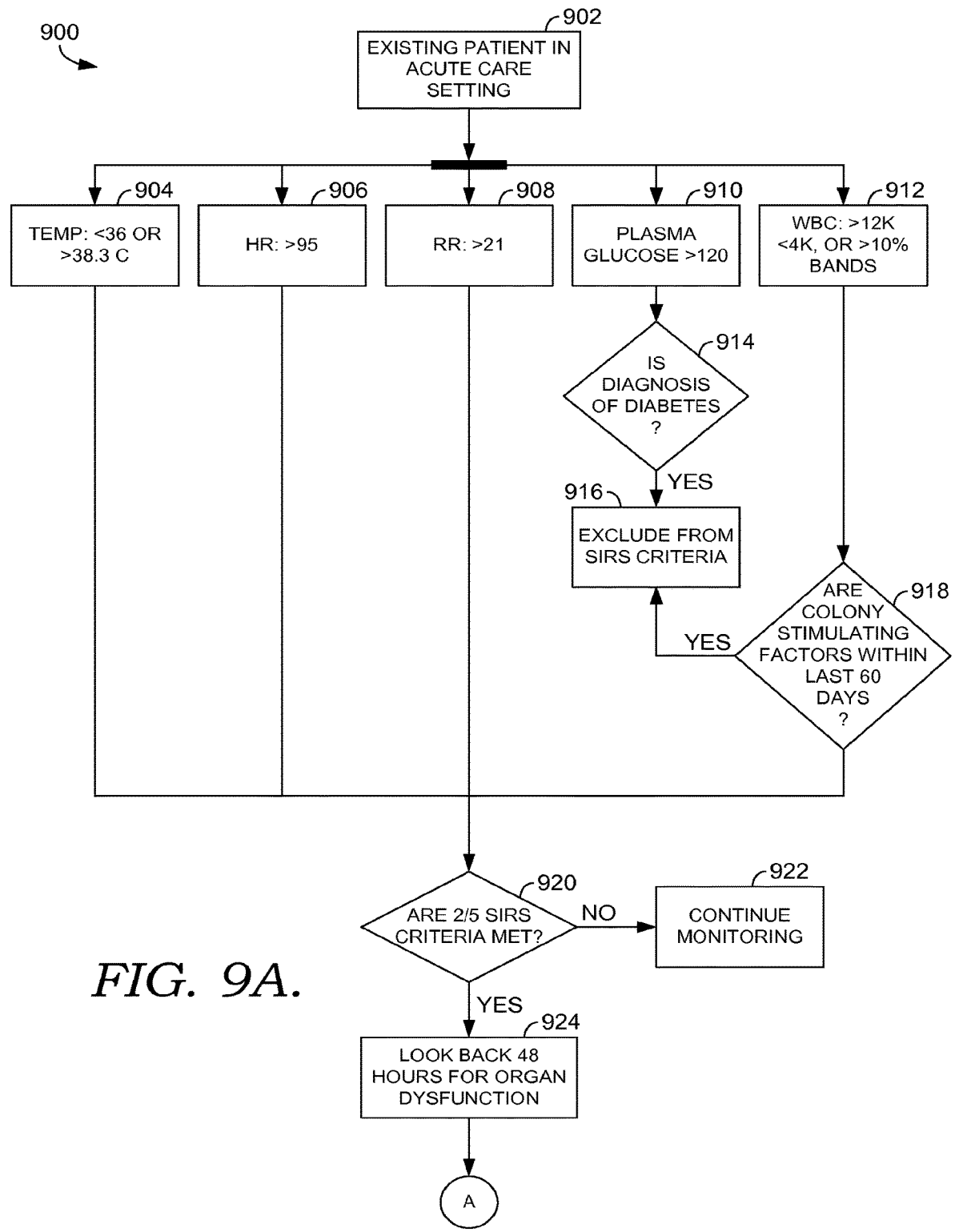
FIGS. 9A and 9B are flow diagrams of an exemplary algorithm of early detection logic using multi-site surveillance and decision support, in accordance with embodiments of the present invention.
Figure 9B:
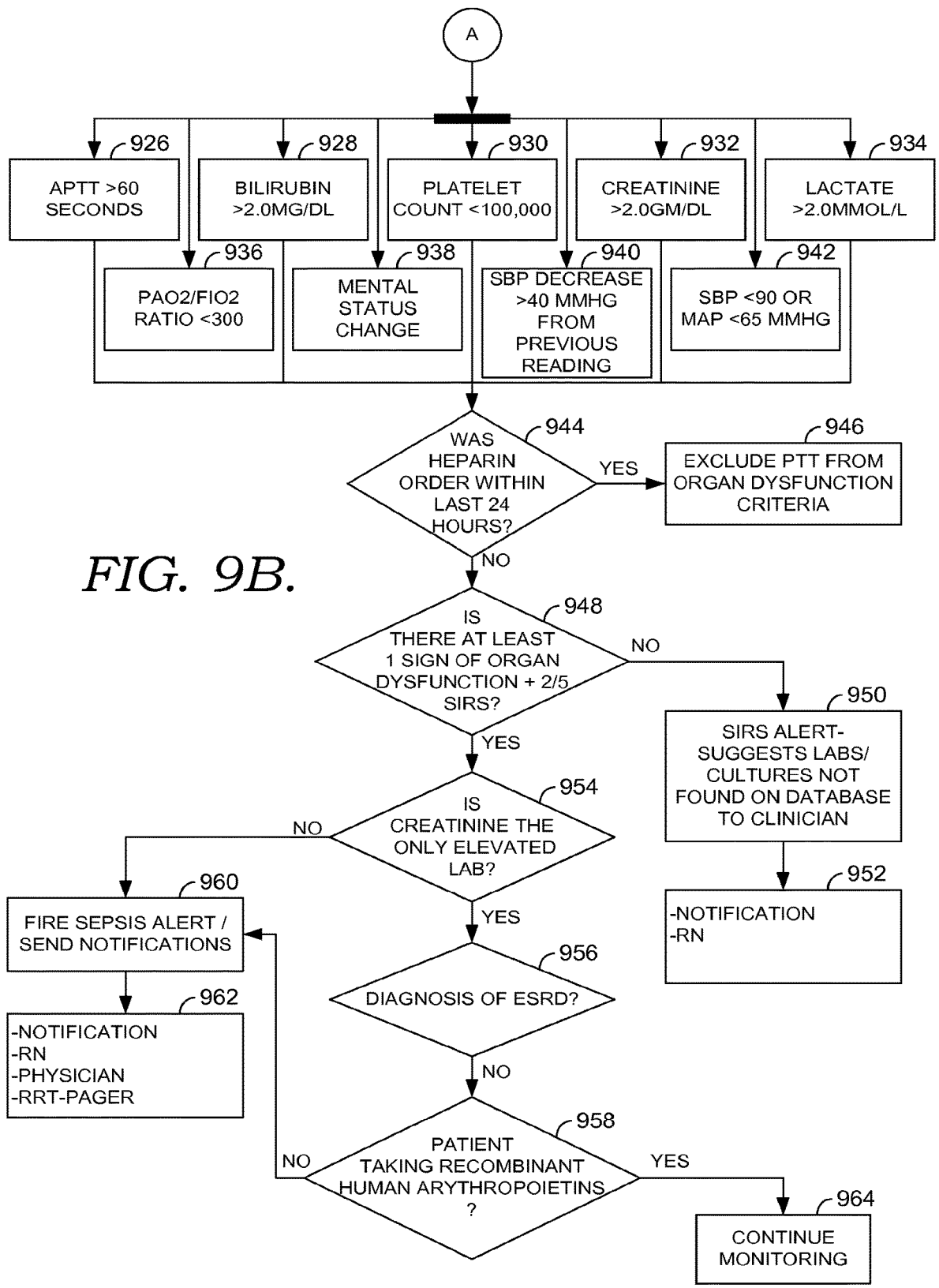

Turning now to FIGS. 9A and 9B, flow diagrams of an exemplary algorithm are illustrated of early detection logic using multi-site surveillance and decision support, in accordance with embodiments of the present invention. The algorithm illustrated in FIGS. 9A and 9B is specific for detecting that a patient is at risk for developing sepsis.

Sepsis occurs in the presence of an infection with a systemic inflammatory response syndrome (SIRS) response. SIRS is a specific consequence to an infection, trauma, burn, or other offense. Sepsis affects nearly 750,000 Americans annually, resulting in a mortality rate of 28.6%. Each case of sepsis costs an additional $43,000 per case and extends the patient length of stay by an average of eleven days. Sepsis rates in the United States are expected to reach an incidence of one million cases a year by 2020. Annually, more Americans die from sepsis than either heart attack or stroke. Early detection is particularly important for sepsis because of the high-mortality rate and also because sepsis is difficult to diagnose, as fever, rapid pulse, and respiratory difficulties are found in many other disorders.

Initially, an existing patient is in an acute care setting, shown at box 902. The criteria typically used initially for detecting risk of sepsis includes the patient's temperature, heart rate, respiratory rate, glucose level, blood glucose (capillary), and white blood cell count. As shown in the exemplary algorithm, at box 904, the criteria for temperature is less than 36° C. or greater than 38.3° C. The criteria for heart rate at box 906 is greater than 95 bpm. The criteria for respiratory rate is greater than 21 breaths per minute, shown at box 908. The criteria for plasma glucose is greater than 120 mg/dL, shown at box 910. At box 912, the white blood cell count criteria is greater than 12,000 per mcL, less than 4,000 per mcL, or greater than 10% bands. For the plasma glucose at box 910, it is determined, at step 914, whether there has been a diagnosis of diabetes, as this affects the patient's blood/plasma sugar levels. If so, the glucose levels are excluded from the criteria for SIRS at step 916. For the white blood cell count at step 912, it is determined whether there have been colony stimulating factors within the previous 60 days at step 918. If so, the white blood cell count is excluded from the SIRS criteria. At step 920, it is determined whether at least two of the five SIRS criteria have been met. If not, the patient continues to be monitored at step 922. If at least two of the five SIRS criteria have been met, at step 924, organ dysfunction is analyzed from the previous 48 hours.

Continuing to FIG. 9B, organ dysfunction utilized several factors, including, but not limited to lactic acid level, systolic blood pressure, mean arterial pressure, creatinine level, bilirubin total, platelet count, neurological symptoms, level of consciousness, whether hallucinations are present, behavior, Glasgow coma score, pediatric coma score, partial thromboplastin time (PTT), and $PaO_2/FiO_2$ ratio. At box 926, the criteria shown for active PTT is greater than 60 seconds. The criteria for bilirubin at box 928 is greater than 2.0 mg/dL. The criteria for platelet count at box 930 is less than 100,000. The criteria for creatinine at box 932 is greater than 2.0 gm/dL. The criteria for lactate at box 934 is greater than 2.0 mmol/L. At box 936, the criteria for the ratio of $PaO_2/FiO_2$ is less than 300. At box 938, it is determined whether or not there has been a mental status change. At box 940, the criteria for systolic blood pressure (SBP) is a decrease of greater than 40 mmHg from the previous measurement or reading. Further, at box 942, an SBP of less than 90 or a mean arterial pressure (MAP) of less than 65 mmHg is the criteria for sepsis. At step 944, it is determined whether heparin was ordered within the last 24 hours. If so, PTT is excluded from the organ dysfunction criteria, shown at step 946.

If heparin was not ordered within the last 24 hours, it is determined, at step 948, whether there was at least one sign of organ dysfunction in addition to two or more out of the five SIRS criteria having been met. If not, a SIRS alert may be communicated at step 950 suggesting to the clinician various other labs and cultures not found on the database. If there is at least one sign of organ dysfunction in addition to at least two of the five SIRS criteria being met, it is determined whether creatinine is the only elevated lab at step 954. If so, it is determined whether the patient has been diagnosed with end stage renal disease (ESRD), shown at step 956. If the patient has not been diagnosed with ESRD, it is determined, at step 958, whether the patient is taking recombinant human arythropoietins. If so, the patient continues to be monitored at step 964. If either creatinine is the only elevated lab, determined at step 954, or the patient is not taking recombinant human arythropoietins, determined at step 958, a sepsis alert is communicated at step 960, which may include one or more of alerts and notifications to the various medical organizations, patient, primary care physician, etc. At step 962, notifications are communicated to one or more providers, including nurses, physicians, or other medical personnel and clinicians. As mentioned, alerts and notifications may be communicated through various mediums, including telephones, pagers, computers, PDAs, fax machines, or the like.

FIG. 10 illustrates a table 1000 including exemplary actionable criteria and alerts for a patient being at risk for developing sepsis, in accordance with embodiments of the present invention. The table 1000 illustrates a results area 1010 indicting that two of five SIRS criteria are present, and that there is no organ dysfunction. The SIRS box 1012 illustrates the criteria for determining whether a patient is at risk for developing SIRS. For example, heart rate and temperature of the patient have been determined to put the patient at risk for SIRS, as the numerical values of these criteria have been met. Respiration, glucose, and the white blood cell count have been determined to be within normal limits. The organ dysfunction box 1014 illustrates that all tests are within the normal limits, including lactate, creatinine, platelet count, bilirubin, PTT, systolic blood pressure, mean arterial pressure, mental status change, and the $PiO_2/FiO_2$ ratio. Next, the alert box 1016 indicates that an alert has been communicated to the medical organizations whose clinicians have treated the patient, the patient, the primary care physician, and/or the like. Here, the alert states that the patient has met SIRS criteria that are listed in the alert. It also states that the physician should be contacted and it also suggests several laboratory tests that can be performed on the patient to further assess the patient's risk for developing SIRS and sepsis. These tests include lactate, creatinine, bilirubin, platelet count, PTT, blood cultures, and UA.

FIG. 11 illustrates a table 1100 including exemplary actionable criteria and alerts for a patient being at risk for developing sepsis, in accordance with embodiments of the present invention. FIG. 11 is similar to FIG. 10 except that the criteria required to send an alert if three of the five SIRS criteria listed have been met based on the patient information, as shown in the results area 1110. Here, the heart rate, temperature, and respirations criteria have been met, as shown under the SIRS box 1112. The organ dysfunction box 1114 indicates that all tests for organ dysfunction are within normal limits. The alert box 1116 indicates that the alert is similar to the alert in FIG. 10, recommending that the physician be contacted and that several laboratory tests be ordered.

FIG. 12 illustrates a table 1200 including exemplary actionable criteria and alerts for a patient being at risk for developing sepsis, in accordance with embodiments of the present invention. FIG. 12 is also similar to FIGS. 10 and 11, but here, as indicated in the results box 1210, organ dysfunction criteria have been met. Like FIG. 10, two of the five SIRS criteria, shown under the SIRS box 1212, have been met, including heart rate and temperature. Under the organ dysfunction box 1214, the lactate measurement is outside of normal limits, and thus the system has indicated that there is a possibility of organ dysfunction. Under the alert box 1216, the alert states that the patient has met criteria for sepsis and organ dysfunction, and that the physician should be notified immediately so that the patient can be evaluated. It also states that early goal directed therapy is essential for the treatment of sepsis, and that treatment is time dependent. In one embodiment, follow-up lab tests are also included in the alert.

FIG. 13 is an exemplary screen display of an alert after determination that a patient is at risk for developing sepsis, in accordance with an embodiment of the present invention. Along with the general alert information on the screen, an alert is shown. Alert area 1310 provides identifying information of the patient to whom the alert concerns. This area also indicates that the patient has met the criteria for being at risk for developing sepsis and states that the patient should be evaluated further. Alert area 1312 indicates that the patient has met a certain number of the SIRS criteria and outlines suggested laboratory tests that would be useful in further evaluating and treating the patient. Alert area 1314 provides the clinician with a useful outline of when the patient met each of the criteria, and if applicable, the numerical result for each criteria. Similarly, organ dysfunction criteria is shown, along with the date and results, if applicable. Some criteria may not have a numerical result, but instead may be a yes or no scenario. For instance, a box of the array may be "turned on" if the patient has a change in his or her mental condition. There may not be a numerical value that can be used in instances such as these. While FIG. 13 illustrates an exemplary alert, it should be noted that this is just one form of an alert that may be communicated when it is determined that a patient is at risk for developing a particular disease or condition, such as sepsis.

Figure 14:
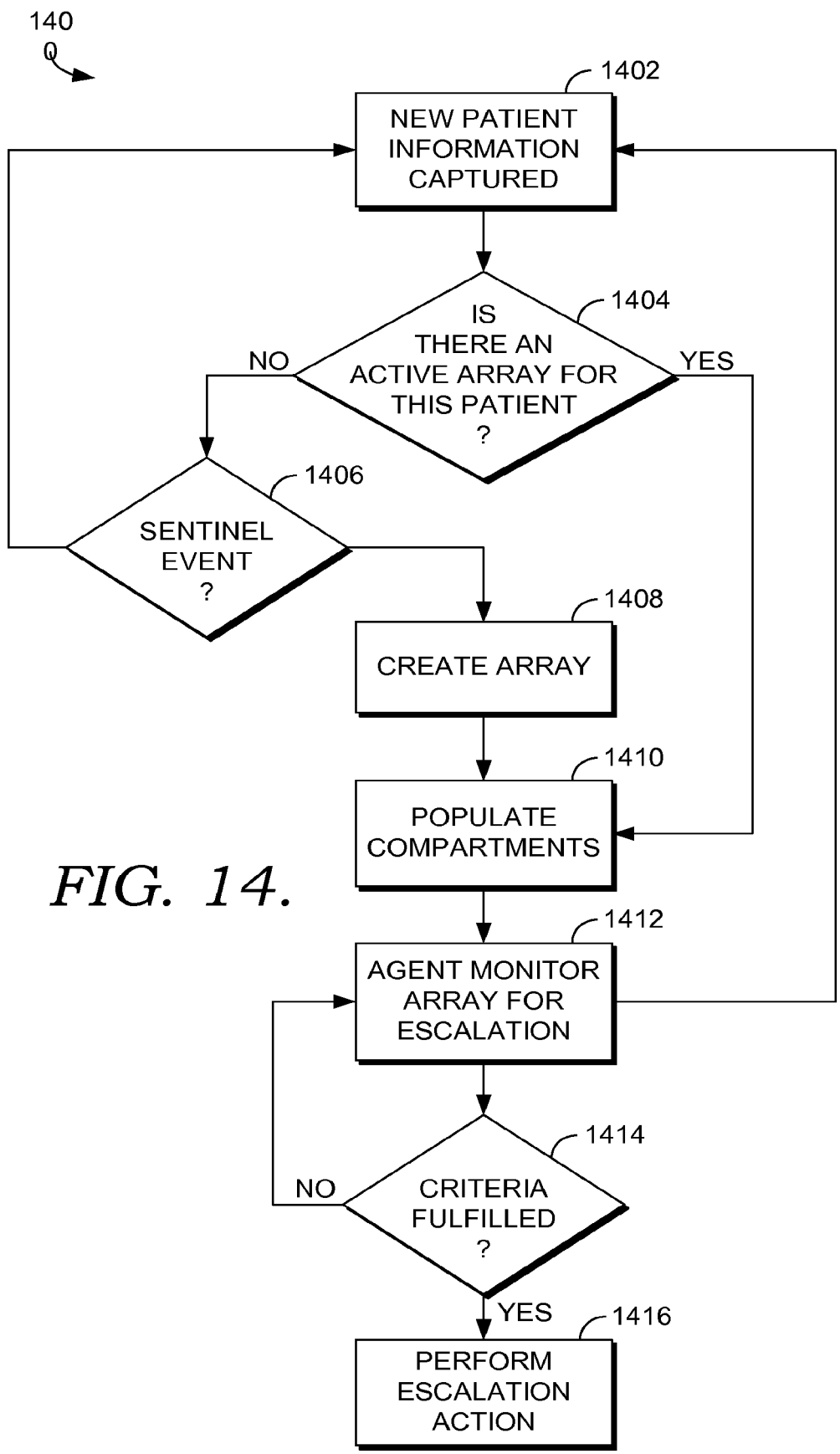
FIG. 14 is a flow diagram showing a method for monitoring patient information received from multiple sites in accordance with an embodiment of the present invention.

Referring next to FIG. 14, a flow diagram of a computer-implemented method 1400 for creating a multi-site persistent array of patient information and monitoring such information is provided. Initially, as shown at block 1402, patient information is received by the manager 202 of FIG. 2 from a medical organization. At step 1404, it is determined whether there are one or more active arrays for the patient for whom patient information is received. For example, it may be determined whether a patient who is running a fever of 101.5 has an active array in the manager 202 for sepsis and/or infection risk. If an array does not exist for the patient for a particular condition, at step 1406, it is determined that an array should exist for a particular piece of information (sentinel event) received for the patient. For example, the system may determine that a patient running a fever of 101.5 degree F. should have an array. At step 1408, the array for the patient for the identified potential condition or state is created.

At step 1410, the nodes or compartments of the array created are populated with relevant patient values and information. For example, if a fever is an identified node for sepsis, the value of the node for fever may be populated in the node or the node may be turned to positive for fever. The system continuously monitors for additional patient information coming for the patient with the open array and monitors the incoming patient information from different organizations for escalation over the defined period of time for the condition or state array. For example, a patient with a sepsis array may be continuously monitored for patient information related to risk factors for sepsis including, but not limited to, fever, rapid heart rate, rapid respiratory rate, elevated white blood cells, and elevated glucose.

At step 1414, it is determined whether a set number of nodes or patient criteria for the identified state or condition have been filled. If not, the system continues to monitor patient information for the array for escalation at step 1412. If it is determined that a set number of nodes or patient criteria received from multiple organizations have been fulfilled, the system performs escalation actions at step 1416 discussed above including alerting the provider and/or collecting patient information and records for presentation upon the next patient event.

Figure 15:
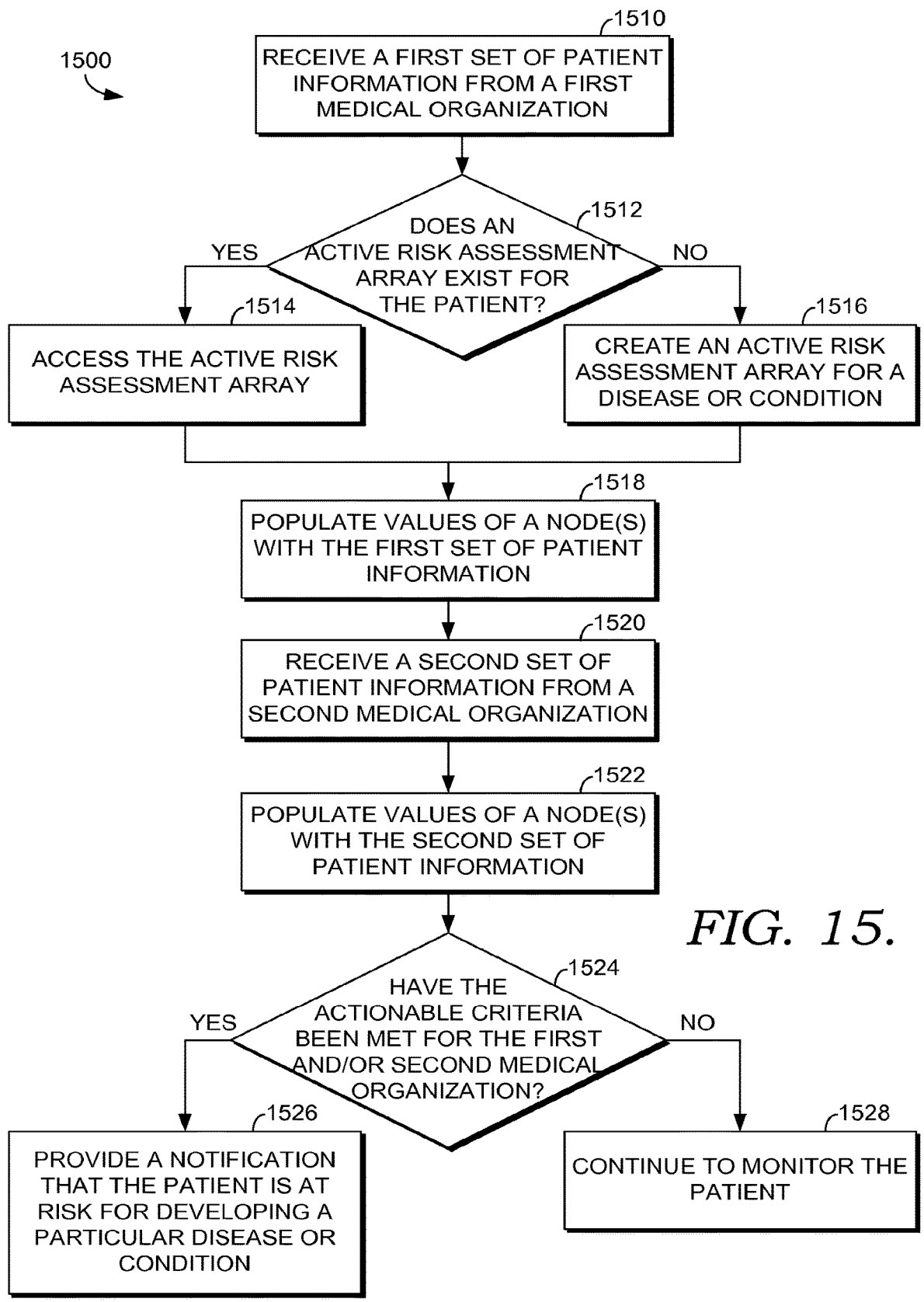
FIG. 15 is a flow diagram showing a method for enabling multi-site surveillance and decision support for a patient's medical care, in accordance with an embodiment of the present invention.

FIG. 15 is a flow diagram showing a method 1500 for enabling multi-site surveillance and decision support for a patient's medical care, in accordance with an embodiment of the present invention. Initially at step 1510, a first set of patient information is received from a first medical organization. This set of patient information may include any number of types of information, including vitals, test results, mental conditions, physical conditions, etc. At step 1512, it is determined whether an active risk assessment array exists for the patient with which the patient information corresponds. As mentioned, an active risk assessment array, or simply an array, may exist for a particular disease or condition. Different arrays may have different nodes or categories that receive different types of patient information. For instance, for sepsis, a patient's temperature may be an important factor and one of the criteria used to determine whether a patient is at risk for sepsis, but for substance abuse, a patient's temperature may be irrelevant. Further, arrays may exist for a predetermined amount of time, which may vary from hours to years, depending on the disease or condition represented by the array. For instance, an array for sepsis may exist for 24-48 hours, while an array for substance abuse or a mental condition may persist in the system for several years. As such, step 1512 of determining whether an active array exists may go even further to determine whether the patient information received is even related to the array, if an array currently exists for the patient.

If it is determined that an active array currently exists, the array is accessed by the system at step 1514. If not, an active risk assessment array may be created at step 1516 for a particular disease or condition. At this point, it may not be known what the patient is at risk for developing, and as such more than one array may be created so that the patient can be monitored for multiple diseases or conditions for which he or she may be at risk for developing. If the patient, based upon a previous condition or a previous operation, may be at risk for developing SIRS or sepsis, an array corresponding to these conditions may be created. At step 1518, values of one or more nodes are populated with the first set of patient information or at least a portion thereof, as some of the information may not be relevant or necessary for use with an array. Values of a node may include numerical values (e.g., a patient's temperature, heart rate, lab test results), alpha-numerical values, or simply may be turned "on" or "off" if the node represents whether the patient has a mental condition or does not, for example. Or, even if the node represents a patient's temperature, the node may be turned "on" or "off" depending on whether the patient's temperature meets the criteria or not.

At step 1520, a second set of patient information is received from a second medical organization. In one embodiment, the first and second medical organizations have distinct medical record systems, such as different companies that store and monitor their medical records. The second set of patient information may represent the patient's visit to a healthcare facility for something related to the visit that produced the first set of patient information, or for something completely unrelated. Even if unrelated, the patient information may turn out to be related as being used in a single array to make the determination that the patient is at risk for a particular disease or condition. At step 1522, the values of one or more nodes are populated with the second set of patient information, or at least a portion thereof. It is determined at step 1524 whether actionable criteria have been met for the first and/or second medical organization. In one embodiment, the monitoring system determines the criteria that are to be used, but in an alternative embodiment, each medical organization is able to establish its own criteria. As such, the first medical organization may receive an alert before the second medical organization if the criteria of the first medical organization are generally more stringent and conservative. In this scenario, the second medical organization may at least receive a notification indicating that the first medical organization received an alert based on its criteria. In some instances, this may prompt the second medical organization to reevaluate and determine whether it needs to further evaluate the patient for the particular disease or condition. When the criteria of the second medical organization are met, the second medical organization would then receive an alert.

If the actionable criteria have been met at step 1526, a notification is provided that the patient is at risk for developing a particular disease or condition. The notification may comprise an alert, and may take on one of many forms, as previously mentioned. If the actionable criteria have not been met, the patient continues to be monitored at step 1528 by way of the active risk assessment array. In one embodiment, the criteria are sepsis-specific actionable criteria, as they apply specifically to sepsis. The nodes of this array specific to sepsis may include, for example, a heart rate, body temperature, respiration rate, white blood cell count, glucose, bands, lactate level, systemic blood pressure, mean arterial pressure, oxygen saturation, creatinine, bilirubin, platelet count, partial thromboplastin time (PTT), and $PaO_2/FiO_2$ ratio.

While FIG. 15 illustrates two medical organizations that send patient information, any number of medical organizations may send patient information. For instance, in one embodiment, a third set of patient information is received from a third medical organization that maintains a different medical record system than the first and second medical organizations. The third set of patient information is associated with the first and second sets based on knowledge that they correspond to the common patient. Values of a third set of nodes of the active risk assessment array are populated with the third set of patient information.

As can be understood, embodiments of the present invention provide action-based deeplinks for search results. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages, which are obvious and inherent to the system and method. It will be understood that certain features and subcombinations are of utility and may be employed without reference to other features and subcombinations. This is contemplated by and is within the scope of the claims.

What is claimed is:

1. A method carried out by a computing device having a processor and a memory, the method being for detecting sepsis in a patient based on multi-site surveillance, the method comprising:

receiving, from a first client application residing on at least one computing device associated with a first medical organization, a first set of patient information that corresponds to the patient who has received medical treatment at the first medical organization and comprises at least a first parameter, wherein the first set of patient information includes a first actionable criteria for the patient being at risk for the sepsis;

receiving, from a second client application residing on at least one computing device associated with a second medical organization, a second set of patient information that corresponds to the patient who has received medical treatment at the second medical organization and comprises at least a second parameter, wherein the first medical organization and the second medical organization are disparate and maintain separate medical record systems, wherein the second set of patient information is for the same patient as the first set of patient information and includes a second actionable criteria for the patient being at risk for the sepsis, and wherein the first medical organization and the second medical organization send information to a cloud computing platform and not directly between one another;

reconciling, by using a cross-venue recognition algorithm, the first set of patient information and the second set of patient information, wherein the reconciling is done by processing the first set of patient information and the second set of patient information to enable a remote centralized cross-venue patient information management, wherein the reconciling includes at least:

processing the first parameter represented by a first medical term used by the first medical organization, processing the second parameter represented by a second medical term different from the first medical term and used by the second medical organization, the first parameter and the second parameter corresponding to a same health condition of the patient, and reconciling the first medical term and the second medical term;

determining that a triggering event has occurred based on at least one from among the first set of patient information and the second set of patient information;

based on occurrence of the triggering event, creating a multi-site risk assessment array for the patient that is related to the triggering event, wherein the multi-site risk assessment array comprises a plurality of nodes and represents the patient's risk of developing the sepsis, and wherein each node of the plurality of nodes represents a distinct health parameter for the sepsis;

populating at least a first portion of the plurality of nodes of the multi-site risk assessment array with at least a portion of the reconciled first set of patient information;

populating at least a second portion of the plurality of nodes of the multi-site risk assessment array with at least a portion of the reconciled second set of patient information, wherein the multi-site risk assessment array for the patient is open and active for a predetermined period of time within which the sepsis can occur in the patient;

continuously monitoring and continuously populating the plurality of nodes of the multi-site risk assessment array, while the multi-site risk assessment array remains open and active, with reconciled medical information of the patient received via the first client application and the second client application, respectively;

determining that sepsis-specific actionable criteria have been met based on at least values of a first node and a second node of the multi-site risk assessment array, among the plurality of nodes; and triggering an escalation logic for providing a near real-time electronic notification including an alert and electronically communicating the near real-time electronic notification including the alert to a present medical provider that the sepsis-specific actionable criteria has been met, wherein the sepsis-specific actionable criteria is the first actionable criteria and the near real-time electronic notification including the alert is communicated to the first medical organization via the first client application and a second near real-time electronic notification is sent to the second medical organization via the second client application and indicates that the near real-time electronic notification including the alert was sent to the first medical organization based on the first actionable criteria.

2. The method of claim 1, wherein each of the first node and the second node represent one or more of a heart rate, a body temperature, a respiration rate, a white blood cell count, glucose, bands, lactate level, systemic blood pressure, mean arterial pressure, oxygen saturation, creatinine, bilirubin, platelet count, partial thromboplastin time (PTT), or a $PaO_2/FiO_2$ ratio.

3. The method of claim 1, wherein the multi-site risk assessment array representing the patient's risk of developing the sepsis remains active for 24 to 72 hours.

4. The method of claim 1, wherein the near real-time electronic notification is provided to each of the first medical organization and the second medical organization such that providers who treated the patient at each of the first medical organization and the second medical organization are alerted as to the patient meeting the sepsis-specific actionable criteria.

5. The method of claim 1, wherein the near real-time electronic notification is further provided to the patient so that the patient can take further action.

6. The method of claim 1, wherein the near real-time electronic notification is further provided to a primary care provider associated with the patient.

7. The method of claim 1, further comprising accessing a database associated with the first medical organization to retrieve the first set of patient information.

8. The method of claim 1, further comprising:
determining that the second actionable criteria set by the second medical organization have not been met.

9. The method of claim 1, wherein the near real-time electronic notification is provided by communicating the near real-time electronic notification to all providers with documented patient contact during the predetermined period of time that the multi-site risk assessment array has been active.

10. The method of claim 1, further comprising providing a recommended care plan to one or more providers based on the first set of patient information and the second set of patient information.

11. One or more non-transitory computer storage media having computer-executable instructions embodied thereon which, when executed by a computing system having a processor and a memory, cause the computing system to perform a method for enabling multi-site surveillance and decision support for a patient's medical care, the method including:

receiving, from a first client application residing on at least one computing device associated with a first medical organization, a first set of patient information that corresponds to a patient who has received medical treatment at the first medical organization and comprises at least a first parameter, wherein the first set of patient information includes a first actionable criteria for the patient being at risk fora sepsis;

receiving, from a second client application residing on at least one computing device associated with a second medical organization, a second set of patient information that corresponds to the patient who has received medical treatment at the second medical organization; and comprises at least a second parameter, wherein the first medical organization and the second medical organization are disparate and maintain separate medical record systems, wherein the second set of patient information is for the same patient as the first set of patient information and includes a second actionable criteria for the patient being at risk for the sepsis, and wherein the first medical organization and the second medical organization send information to a cloud computing platform and not directly between one another;

reconciling, by using a cross-venue recognition algorithm, the first set of patient information and the second set of patient information, wherein the reconciling is done by processing the first set of patient information and the second set of patient information to enable a remote centralized cross-venue patient information management, wherein the reconciling includes at least:

processing the first parameter represented by a first medical term used by the first medical organization, processing the second parameter represented by a second medical term different from the first medical term and used by the second medical organization, the first parameter and the second parameter corresponding to a same health condition of the patient, and reconciling the first medical term and the second medical term;

determining that a triggering event has occurred based on at least one from among the first set of patient information and the second set of patient information;

based on occurrence of the triggering event, creating a multi-site risk assessment array for the patient that is related to the triggering event, wherein the multi-site risk assessment array comprises a plurality of nodes and represents the patient's risk of developing the sepsis, and wherein each node of the plurality of nodes represents a distinct health parameter for the sepsis;

populating at least a first portion of the plurality of nodes of the multi-site risk assessment array with at least a portion of the reconciled first set of patient information;

populating at least a second portion of the plurality of nodes of the multi-site risk assessment array with at least a portion of the reconciled second set of patient information, wherein the multi-site risk assessment array for the patient is currently open and active for a predetermined period of time within which the sepsis can occur in the patient;

continuously monitoring and continuously populating the plurality of nodes of the multi-site risk assessment array, while the multi-site risk assessment array remains open and active, with reconciled medical information of the patient received via the first client application and the second client application, respectively;

determining that sepsis-specific actionable criteria have been met based on at least values of a first node and a second node of the multi-site risk assessment array, among the plurality of nodes; and triggering an escalation logic for providing a near real-time electronic notification including an alert and electronically communicating the near real-time electronic notification including the alert to a present medical provider that the sepsis-specific actionable criteria has been met, wherein the sepsis-specific actionable criteria is the first actionable criteria and the near real-time electronic notification including the alert is communicated to the first medical organization via the first client application and a second near real-time electronic notification is sent to the second medical organization via the second client application and indicates that the near real-time electronic notification including the alert was sent to the first medical organization based on the first actionable criteria.

12. The one or more non-transitory computer storage media of claim 11, wherein the determination that the patient has met the sepsis-specific actionable criteria for developing the sepsis is made by execution of an algorithm.

13. The one or more non-transitory computer storage media of claim 11, wherein the first medical organization and the second medical organization each have different sets of actionable criteria for the patient being at risk for developing the sepsis.

14. The one or more non-transitory computer storage media of claim 13, wherein the second medical organization is not notified by an alert if the second actionable criteria set by the second medical organization have not yet been met.

15. The one or more non-transitory computer storage media of claim 11, wherein the sepsis-specific actionable criteria for the patient being at risk for developing the sepsis is met when numerical values of a predetermined quantity of nodes of the multi-site-risk assessment array exceed a predetermined threshold.

16. The one or more non-transitory computer storage media of claim 11, wherein the sepsis-specific actionable criteria for the patient being at risk for developing the sepsis are met when a predetermined quantity of nodes are in an on state.

17. A computerized multi-site decision support system for detecting a sepsis in a patient based on multi-site surveillance, the computerized multi-site decision support system comprising:

one or more processors; and one or more computer storage media storing computer readable instructions that, when executed by the one or more processors, cause the one or more processors to perform a method including:

receiving, from a first client application residing on at least one computing device associated with a first medical organization, a first set of patient information that corresponds to the patient who has received medical treatment at the first medical organization and comprises at least a first parameter, wherein the first set of patient information includes a first actionable criteria for the patient being at risk for the sepsis;

receiving, from a second client application residing on at least one computing device associated with a second medical organization, second set of patient information that corresponds to the patient who has received medical treatment at the second medical organization and comprises at least a second parameter, wherein the first medical organization and the second medical organization are disparate and maintain separate medical record systems, wherein the second set of patient information is for the same patient as the first set of patient information and includes a second actionable criteria for the patient being at risk for the sepsis, and wherein the first medical organization and the second medical organization send information to a cloud computing platform and not directly between one another;

reconciling, by using a cross-venue recognition algorithm, the first set of patient information and the second set of patient information wherein the reconciling is done by processing the first set of patient information and the second set of patient information to enable a remote centralized cross-venue patient information management, wherein the reconciling includes at least:

processing the first parameter represented by a first medical term used by the first medical organization, processing the second parameter represented by a second medical term different from the first medical term and used by the second medical organization, the first parameter and the second parameter corresponding to a same health condition of the patient, and reconciling the first medical term and the second medical term;

determining that a triggering event has occurred based on at least one from among the first set of patient information and the second set of patient information;

determining whether an open and active a multi-site risk assessment array for the sepsis associated with the triggering event that is open and active currently exists for the patient, wherein the multi-site risk assessment array for the patient is open and active for a predetermined period of time within which the sepsis can occur in the patient;

if the multi-site risk assessment array for the sepsis associated with the triggering event that is open and active currently exists for the patient, accessing the multi-site risk assessment array;

if the multi-site risk assessment array for the sepsis associated with the triggering event that is open and active currently does not exist for the patient, building a multi-site risk assessment array for the sepsis for which the patient needs to be monitored and activating and opening the multi-site risk assessment array;

populating values of a first set of nodes of the multi-site risk assessment array with the reconciled first set of patient information;

populating values of a second set of nodes of the multi-site risk assessment array with the reconciled second set of patient information;

based on the multi-site risk assessment array, algorithmically determining that the first actionable criteria set by the first medical organization indicating that the patient is at risk for developing the sepsis have been met; and electronically communicating a first electronic notification to the first medical organization in near real-time including an alert that the patient is at risk for the sepsis and electronically communicating a second electronic notification to the second medical organization in near real-time indicating that the first electronic notification including the alert was sent to the first medical organization based on meeting the first actionable criteria set by the first medical organization indicating to indicate that the patient is at risk for developing the sepsis.

18. The computerized multi-site decision support system of claim 17, wherein the method further includes:
- receiving a third set of patient information, which corresponds to the same patient, from a third medical organization that maintains a medical record system different the medical record system of the first medical organization and the medical record system of the second medical organization;
- associating the third set of patient information with the first set of patient information and the second set of patient information based on the patient; and
- populating the values of a third set of nodes of the multi-site risk assessment array with the third set of patient information.

* * * * *